(12) United States Patent
Lee

(10) Patent No.: US 8,398,867 B2
(45) Date of Patent: *Mar. 19, 2013

(54) VIDEO RATE-ENABLING PROBES FOR ATOMIC FORCE MICROSCOPY

(76) Inventor: Chung Hoon Lee, Fresno, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/276,173

(22) Filed: Oct. 18, 2011

(65) Prior Publication Data

US 2012/0090058 A1 Apr. 12, 2012

Related U.S. Application Data

(63) Continuation of application No. 12/011,800, filed on Jan. 30, 2008, now Pat. No. 8,062,535.

(60) Provisional application No. 60/898,492, filed on Jan. 31, 2007.

(51) Int. Cl.
*B44C 1/22* (2006.01)
*C25F 3/00* (2006.01)

(52) U.S. Cl. ............ 216/11; 216/2; 216/79; 216/99

(58) Field of Classification Search ............ 216/11, 216/2, 79, 99
See application file for complete search history.

(56) References Cited

U.S. PATENT DOCUMENTS

| | | | | |
|---|---|---|---|---|
| 5,021,364 | A | * | 6/1991 | Akamine et al. ............ 850/60 |
| 5,066,358 | A | | 11/1991 | Quate |
| 5,264,696 | A | * | 11/1993 | Toda ............ 250/234 |
| 6,198,300 | B1 | | 3/2001 | Doezema et al. |
| 6,274,198 | B1 | | 8/2001 | Dautartas |
| 8,062,535 | B2 | * | 11/2011 | Lee ............ 216/11 |
| 2012/0036602 | A1 | | 2/2012 | Lee |

FOREIGN PATENT DOCUMENTS

DE 4214400 A1 12/1992

OTHER PUBLICATIONS

Supplementary European Search Report issued in European Patent Application No. 08725061.9, mailed on Aug. 17, 2012.
Burger et al., "High Resolution Shadow Mask Patterning in Deep Holes and Its Application to an Electrical Wafer Feed-Through," 8th International Conference on Solid-State Sensors and Actuators, and Eurosensors IX, Stockholm, Sweden, Jun. 25-29, 1995, pp. 573-576.

* cited by examiner

*Primary Examiner* — Roberts Culbert
(74) *Attorney, Agent, or Firm* — The Marbury Law Group PLLC

(57) ABSTRACT

Method for producing a probe for atomic force microscopy with a silicon nitride cantilever and an integrated single crystal silicon tetrahedral tip with high resonant frequencies and low spring constants intended for high speed AFM imaging.

7 Claims, 46 Drawing Sheets

VIDEO RATE-ENABLING PROBES FOR ATOMIC FORCE MICROSCOPY

BACKGROUND OF THE INVENTION

This invention relates to methods for producing probes for use in probe-based instruments, including applications where high-speed imaging (up to video rate) is desired.

For the sake of convenience, the current description focuses on probes that may be realized for a particular embodiment of probe-based instruments, the atomic force microscope (AFM). Probe-based instruments include such instruments as AFMs, 3D molecular force probe instruments, high-resolution profilometers (including mechanical stylus profilometers), surface modification instruments, chemical or biological sensing probes, and micro-actuated devices. The probes described herein may be realized for such other probe-based instruments.

An AFM is an instrument used to produce images of surface topography (and/or other sample characteristics) based on information obtained from scanning (e.g., rastering) a sharp tip on the end of a cantilever relative to the surface of the sample. Topographical and/or other features of the surface are detected by sensing changes in the probe's mechanical response to surface features and using feedback to return the system to a reference state. By scanning the probe relative to the sample, a "map" of the sample topography or other sample characteristics may be obtained.

Changes in the probe's mechanical response are typically detected by an optical lever arrangement whereby a light beam is directed onto the cantilever in the same reference frame as the optical lever. The beam reflected from the cantilever illuminates a position sensitive detector (PSD). As the probe's mechanical response changes, a change in the output from the PSD is induced. These changes in the PSD signal are typically used to trigger a change in the vertical position of the base of the probe relative to the sample (referred to herein as a change in the Z position, where Z is generally orthogonal to the XY plane defined by the sample), in order to maintain a constant pre-set value for one or more of the probe's mechanical responses. It is this feedback that is typically used to generate an AFM image.

AFMs can be operated in a number of different sample characterization modes, including contact mode where the tip of the probe is in constant contact with the sample surface, and AC modes where the tip makes no contact or only intermittent contact with the surface. These two modes define two mechanical responses of the probe that can be used in the feedback loop which allow the user to set a probe-based operational parameter for system feedback.

In contact mode the interaction between the probe and the sample surface induces a discernable effect on a probe-based operational parameter, such as the cantilever deflection. In AC mode the effects of interest include the cantilever oscillation amplitude, the phase of the cantilever oscillation relative to the signal driving the oscillation, or the frequency of the cantilever oscillation. All of these probe-based operational parameters are detectable by a PSD and the resultant PSD signal is used as a feedback control signal for the Z actuator to maintain the designated probe-based operational parameter constant.

The feedback control signal also provides a measurement of the sample characteristic of interest. For example, when the designated parameter in an AC mode is oscillation amplitude, the feedback signal may be used to maintain the amplitude of cantilever oscillation constant to measure changes in the height of the sample surface or other sample characteristics.

Some current AFMs can take images up to 100 um$^2$, but are typically used in the 1-10 um$^2$ regime. Such images typically require 4-10 minutes to acquire. Many efforts are currently being made to move toward video rate imaging. The reasons for these efforts include the desire to image moving samples, to image more ephemeral events and simply to complete imaging on a more timely basis. One important means for moving toward video rate imaging is to decrease the mass of the probe, thereby achieving a lower spring constant with a higher resonant frequency.

Currently, conventional probes are 50-450 μ in length with spring constants of 0.01-200 N/m and fundamental resonant frequencies, $f_R$, of 10-500 kHz. Physical laws put lower limits on the achievable resolution and scan speed of conventional probes, given acceptable noise levels.

To get the best resolution measurements, one wants the tip of the probe to exert only a low force on the sample. In biology, for example, one often deals with samples that are so soft that forces above 10 pN can modify or damage the sample. This also holds true for high resolution measurements on 'hard' samples such as inorganic crystals, since higher forces have the effect of pushing the tip into the sample, increasing the interaction area and thus lowering the resolution. For a given deflection of the probe, the force increases with the spring constant, k, of the probe. When operating in air in AC modes where the tip makes only intermittent contact with the sample surface, spring constants below 30 N/m are desirable. For general operation in fluid, very small spring constants (less then about 0.1 N/m) are desirable.

To get measurements with higher scan speeds, one wants probes with a high $f_R$. After passing over a sample feature, the probe response is about $1/f_R$ seconds for contact mode and $Q/f_R$ seconds for AC modes (where Q is the quality factor for the probe). This sets a fundamental limit on scanning speed: if the response time of the probe is to be lowered, the $f_R$ must be raised.

The thermal noise of a probe involves fixed noise energy (of order kT) spread over a frequency range up to approximately the $f_R$, where k is the Boltzmann constant and T is the temperature in Kelvin. Thus, the higher $f_R$, the lower the noise per unit band width below $f_R$.

The ideal probe for video rate imaging would have a $f_R$ in the 5-10 MHz range. It would also have a force constant in the 1-40 N/m range. Conventional probes would need to shrink an order of magnitude, to approximately 5-8 um in length or width, to achieve this goal.

Probes are microfabricated by using semiconductor integrated circuit fabrication techniques as this provides a way to batch produce probes with consistent cantilever and tip geometries necessary for use with AFMs today. These techniques include, but are not limited to: thin film deposition, photolithography with optical masks, Reactive Ion Etching (RIE) with plasma, wet etching of silicon, and wafer-to-wafer bonding. Silicon and silicon nitride are the two primary semiconductor materials from which AFM probes are fabricated. Silicon probes have thicker cantilevers which give higher resonant frequencies and force constants than silicon nitride probes. This is due to larger thickness variations when etching bulk silicon compared to depositing silicon nitride with Chemical Vapor Deposition (CVD), forcing silicon processes to stop at thicker cantilevers in order to assure higher yields. One can overcome these difficulties by using a Silicon-on-Insulator (SOI) wafer, but this introduces much higher costs. Silicon nitride probes have duller and shorter tips than silicon probes because silicon nitride is deposited in silicon molds which are difficult to machine and work with.

Current probe fabrication processes limit the ability of the person skilled in the art to reproducibly shrink probe lengths to 5-8 um, as well as their ability to shrink probe widths to those dimensions when probe lengths are also relatively small. This is due to a number of factors, including: (i) photolithography alignment issues when processing both sides of a silicon wafer, (ii) wafer bonding alignment issues, or (iii) photolithography variations on drastically uneven wafer surfaces. Probe fabrication processes usually incorporate at least one of these techniques and dimension variations of 5um are not unusual. Furthermore, shorter probes will require the relatively thin cantilevers in order to keep force constants in the range required for AFM. All these factors make current processes unviable for the purpose envisioned here.

SUMMARY OF THE INVENTION

It is therefore an object of the invention to provide an improved AFM probe fabrication process which allows for the production of high-speed cantilevers at or below 8um in length and width, with integral sharp tips and with moderate force constants compatible with AFM at the atomic scale.

The high-frequency low-spring constant probes that are the object of the invention consist of a handle, a cantilever and a sharp tip. Alternative embodiments also include probes without tips where one could add different customized tips as needed or use the tipless cantilever as a force sensor. The handle is formed out of a silicon substrate and has a sloping extending edge in a (111) plane which forms an acute angle with the top of the handle in a (100) plane. The cantilever is formed from a suitable thin film that traverses the sloping (111) edge and extends out in the [110] direction in a (100) plane. The free end of the cantilever has an integrated silicon tip whose base is attached to the (100) plane with the apex protruding generally out and away from the base.

BRIEF DESCRIPTION OF THE DRAWINGS

All the directions and planes of crystallographic notation used in the figures use wafer manufacturers' notations and are intended to be equivalent directions and planes.

FIGS. 401, 402 and 403 show another substrate embodiment where the substrate is a Silicon-on-Insulator (SOI).

DETAILED DESCRIPTION OF THE PREFERRED EMBODIMENTS

Figure 1:
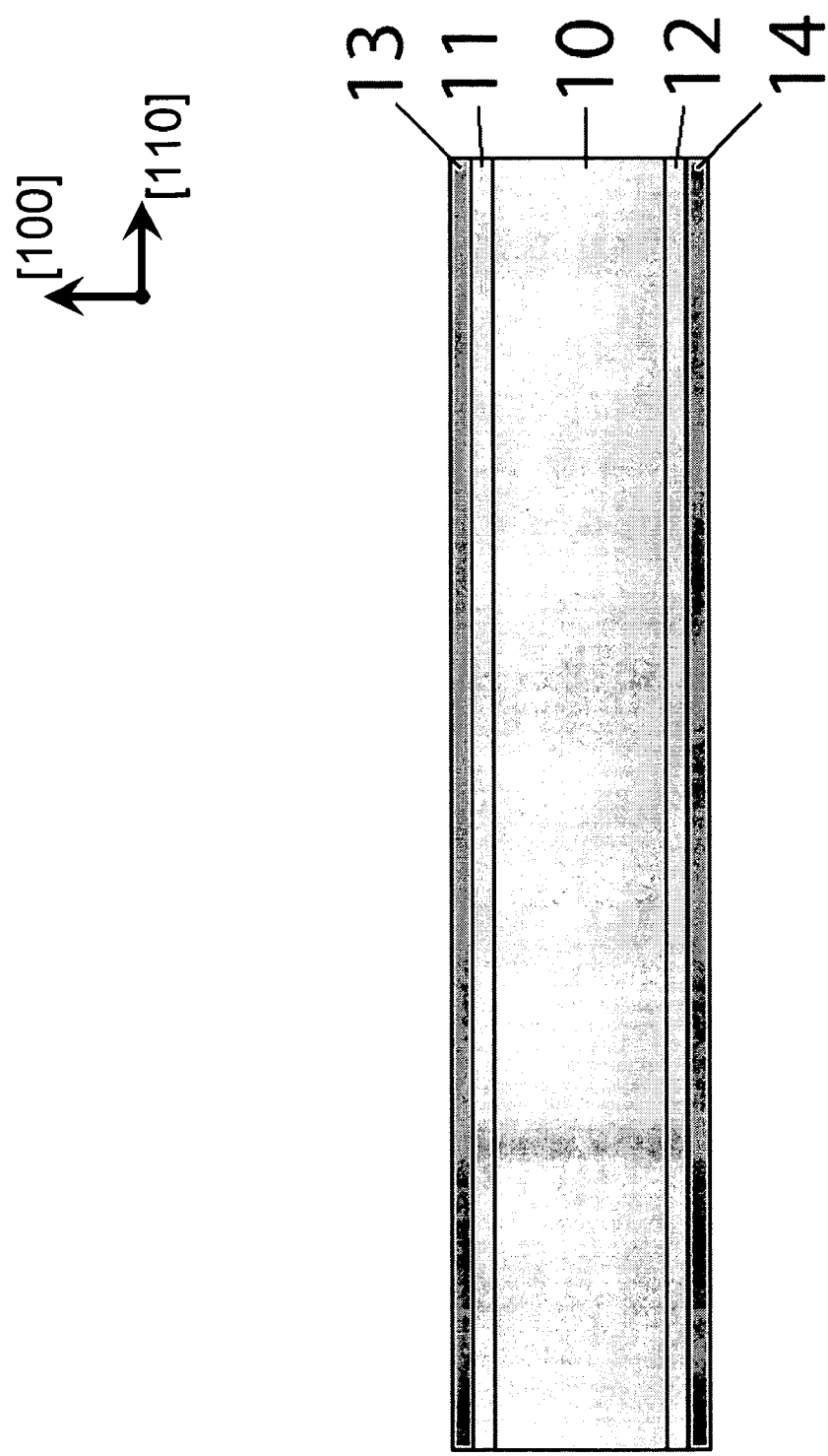
FIG. 1 is a cross-sectional view showing a silicon (100) wafer with silicon dioxide and silicon nitride on each side that forms the starting point of the first embodiment of the present invention.

The process for producing the high-frequency low-spring constant probes that are the object of the invention starts with a (100) silicon substrate, which has a top-side and a bottom-side. A membrane with a (100) surface bound by (111) planes is formed from this substrate by anisotropically wet etching the bottom-side of the silicon substrate which has been masked by a film or films formed via any suitable lithography process. The membrane thickness is chosen, using a timed etch, such that a tip of desired height can be formed from the membrane. The bottom-side of the substrate is coated with a film or films suitable for forming a cantilever. The film or films are formed into the cantilever by aligning a shadow mask to the bottom-side of the silicon substrate relative to the rectilinear intersection of a (111) plane and the (100) plane of the membrane so that a cantilever of controlled length will extend from this intersection and point in the [110] direction. This length can be further reduced in a process which undercut etches the cantilever. This exposes the bottom-side silicon membrane excepting the area covered by the cantilever. The last steps are to form a tip from the silicon membrane.

One tip-formation process is to etch part of the tip from the bottom-side and part from the top-side of the silicon substrate. In this process the exposed bottom-side silicon is anisotropically etched, a processing step which undercut etches the cantilever. The time of the etch will control the height of the tip, while reducing the effective length of the cantilever. The undercut etch is stopped after two intersecting {411} planes in the silicon are formed. These planes become two facets of the tip. The silicon so exposed is oxidized to protect it during subsequent etching. The top-side film or films are then selectively removed to expose the top-side (100) silicon surface. The exposed silicon is anisotropically etched, completely removing the remaining silicon membrane, except a tetrahedral silicon tip formed on the free end of the cantilever. This etch exposes the last facet of the tetrahedral tip, a (111) plane. The final step is to selectively remove any remaining oxide on the wafer via wet etching with an appropriate acid.

Another tip-formation process is to etch the tip entirely from the top-side of the silicon substrate. In this process the exposed bottom-side silicon surrounding the cantilever is oxidized. A top-side to bottom-side lithography tool can be used to pattern a tip etch mask on the top-side film or films relative to the cantilever on the bottom-side of the silicon membrane. A large number of tip shapes can be made by appropriately tailoring the tip etch mask shapes and silicon etch processes. For example, one could use plasma (RIE) and/or wet etching processes, both isotropic and/or anisotropic, to create faceted polyhedron tips or rounded conical tips. In these cases, the etching is stopped when the oxide film and nitride cantilever junction is reached on the bottom-side of the silicon membrane. The final step is to selectively remove any remaining oxide on the wafer via wet etching with an appropriate acid.

Shadow mask techniques are common to those skilled in the art of micromachining. A cantilever shadow mask can easily be produced by micromachining an aperture with the shape of the desired cantilever in a (100) silicon substrate, or any other suitable substrate. A simple lithography and etch on the top-side of the substrate can make a small and controllable cantilever-shaped trench. A simple lithography and thru-substrate etch on the bottom-side of the silicon substrate can turn the trench into the cantilever-shaped aperture.

FIG. 1 shows a cross-sectional view of the first two processing steps of producing the high-frequency low-spring constant probes that are the object of the invention. In the first step, two layers 11 and 12 of thermal silicon dioxide (referred to herein as oxide) film are grown on each surface of a monocrystalline (100) silicon substrate 10. Oxide is preferred because it is pin hole free, uniform, and derives from a generally clean process. The oxide serves to keep the surfaces of the silicon substrate 10 clean, and also serves to protect the silicon surfaces from the Reactive Ion Etch (RIE), which is used to remove portions of silicon nitride film (referred to as nitride herein), as shown in FIG. 2.

In the second processing step of FIG. 1, two layers 13 and 14 of nitride film are deposited on the oxide films 11 and 12, respectively. Either Plasma-Enhanced Chemical Vapor Deposition (PECVD) or Low Pressure Chemical Vapor Deposition (LPCVD) can be used for this step. The nitride can be a stoichiometric film ($Si_3N_4$), though a low-stress variant ($Si_xN_y$) is preferred. Similarly, another material can be used instead of nitride, such as a polymer or any other semiconductor material known to those skilled in the art, as long as it can serve as an etch mask for the wet anisotropic silicon etch shown in FIG. 2.

Figure 2:
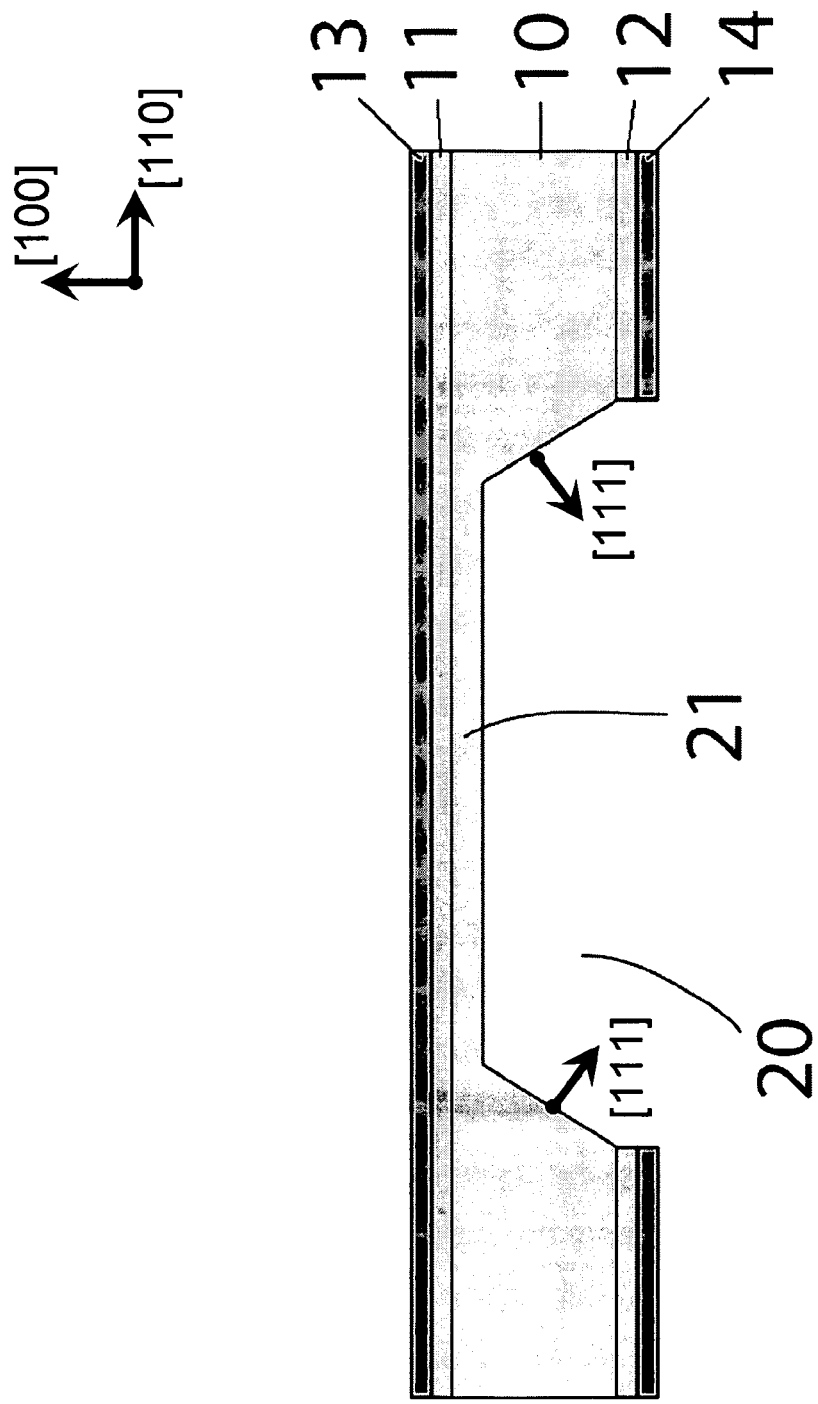
FIG. 2 is a cross-sectional view showing the anisotropic etch of the silicon substrate to form a membrane after patterning an etch mask in the bottom-side films.

FIG. 2 shows a cross-sectional view of the next three processing steps. In the first of these steps, conventional lithography followed by a RIE is used to pattern and then etch a rectangular opening through the bottom nitride film 14; the RIE is stopped when it reaches the underlying oxide film 12. In the second of these steps, a chemical etchant selective to oxide and non-reactive with silicon or nitride, for instance HF or Buffered Oxide Etch (BOE), is used to etch the rectangular opening through the oxide film 12. In the third of these three steps, wet anisotropic silicon etching is used to etch a pit 20 into the silicon substrate 10 and form a thin silicon membrane 21 of the desired thickness by timed etching. Potassium Hydroxide (KOH) is the preferred etchant, though any other suitable anisotropic silicon etchant will suffice. The thickness of the membrane 21 will limit the height of the silicon tip to be included in the probes resulting from completion of all steps described herein to the thickness of the membrane 21 or somewhat less. The patterned nitride film 14 resulting from the first of these three steps serves as an etch mask for this wet anisotropic etching. The four sidewalls of the pit 20 formed in the silicon substrate 10 are {111} crystallographic silicon surfaces.

Figure 3A:
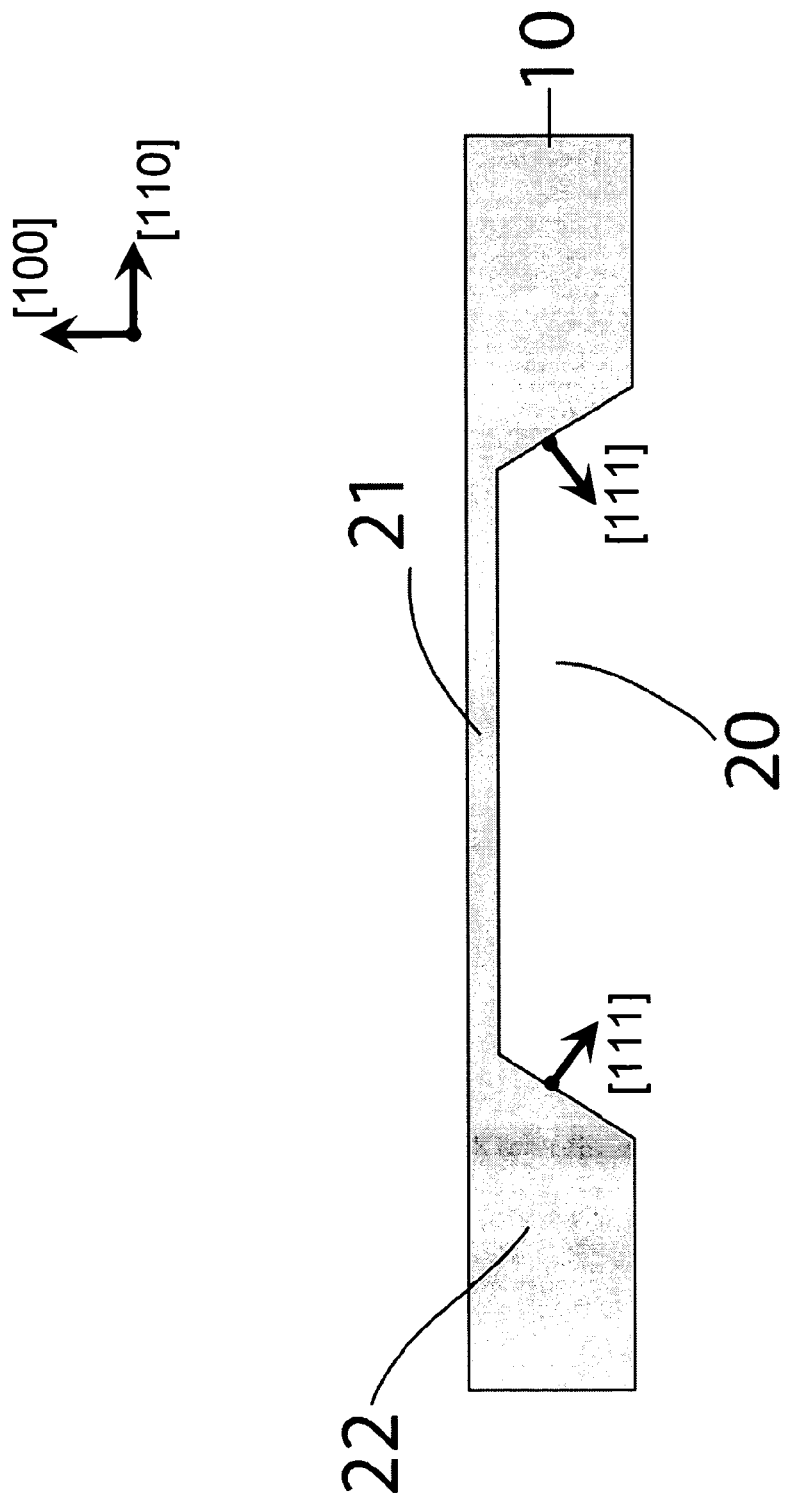
FIGS. 3A and 3B are, respectively, a cross-sectional view and bottom-side plan view of the silicon substrate with membrane after the removal of the silicon nitride and silicon dioxide layers.
Figure 3B:
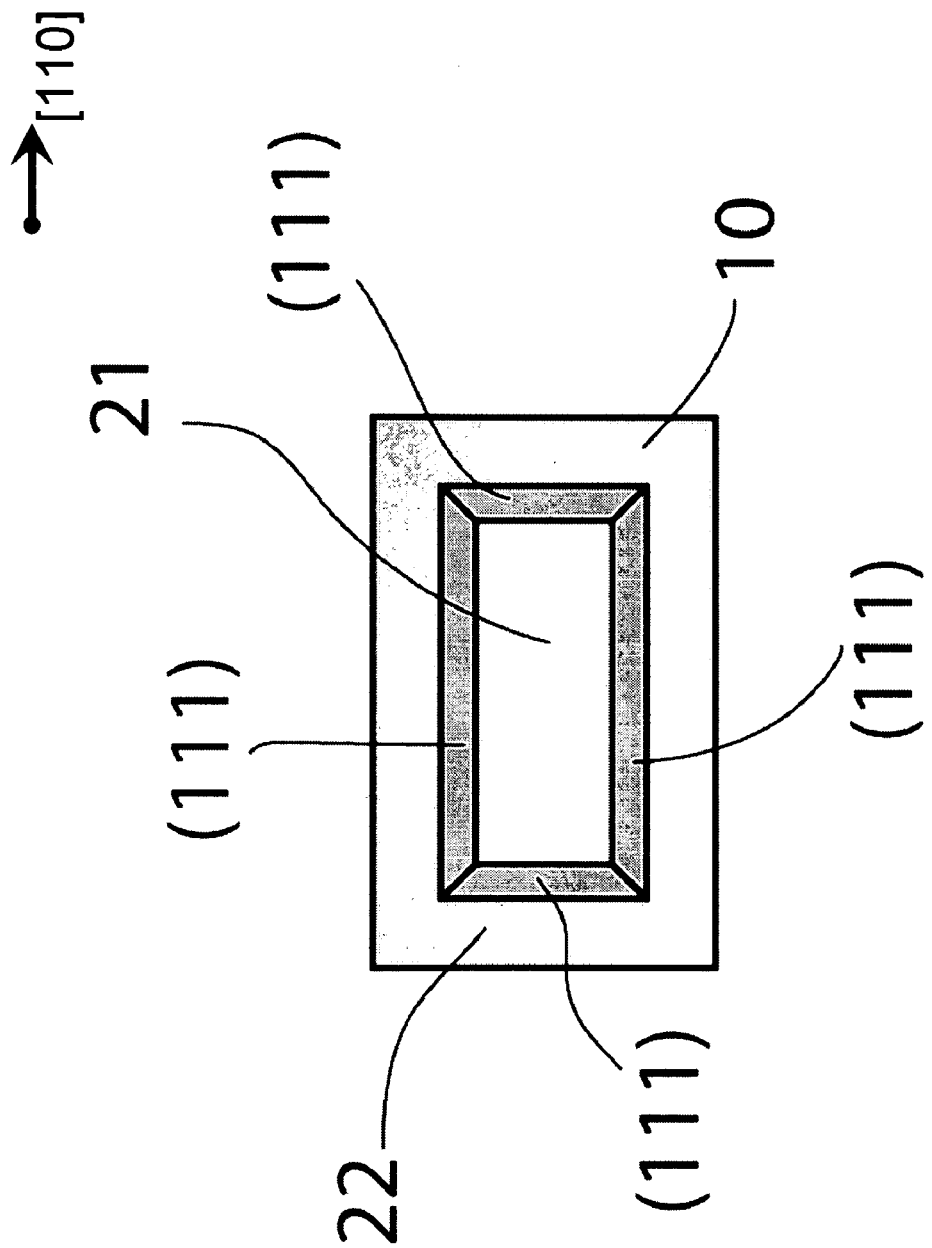

FIG. 3A shows the removal of the remaining nitride films 13 and 14 and oxide films 11 and 12, leaving the bare etched silicon substrate 10. Concentrated HF (49%) can be used to remove all the remaining films simultaneously. Alternatively, boiling phosphoric acid ($H_3PO_4$) could be used to remove the remaining nitride films 13 and 14, and thereafter dilute HF or BOE can be used to remove the remaining oxide films 11 and 12. The remaining silicon substrate 10 can be viewed as three regions of the probes that will result from completion of all steps described herein: 22 will be formed into the silicon handle, 21 will be formed into the tetrahedral silicon tip, and 10 will be the remaining bulk silicon substrate. FIG. 3B shows a bottom-side plan view of the remaining silicon substrate 10 with the rectangular pit 20 resulting from the prior processing steps.

Figure 4:
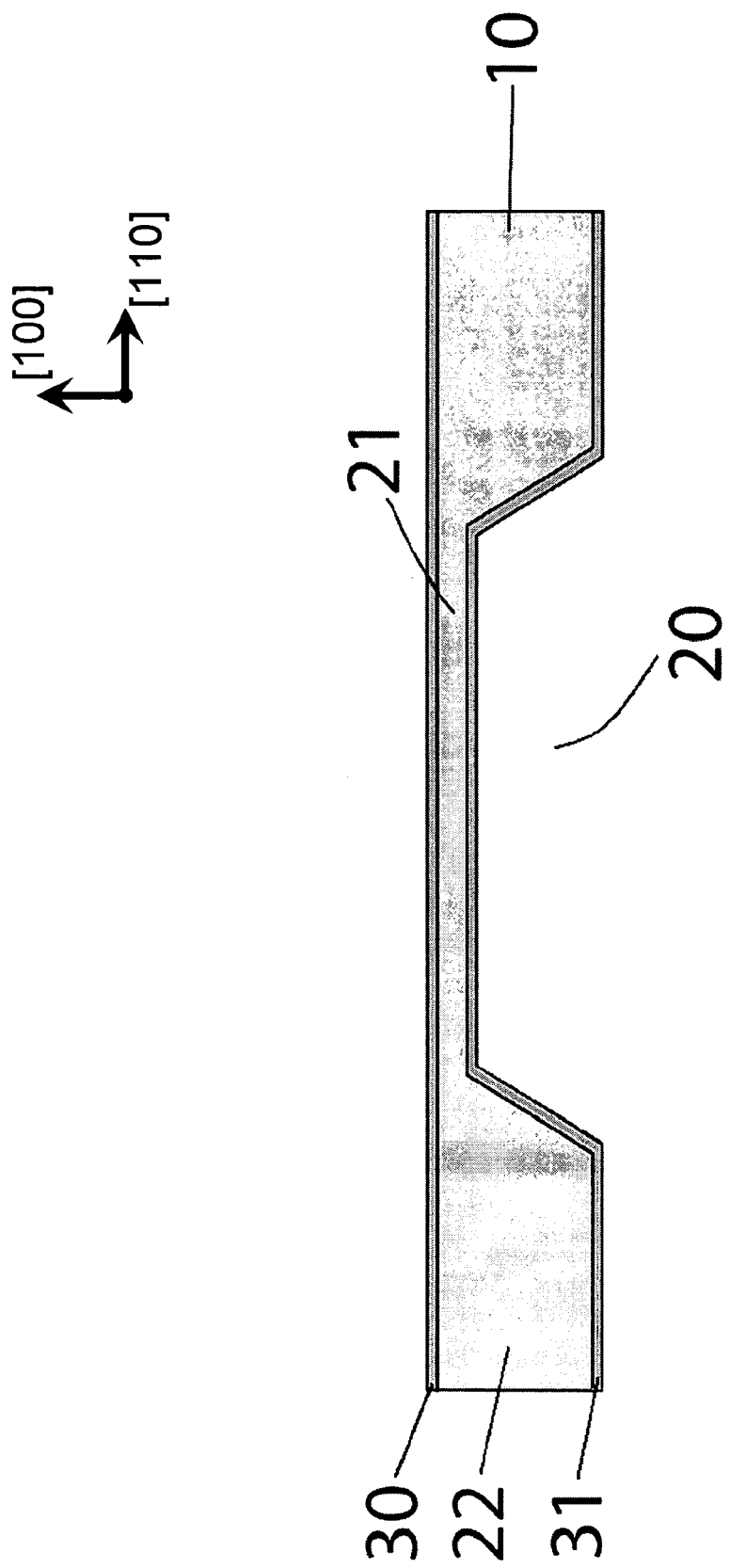
FIG. 4 is a cross-sectional view showing the silicon substrate with membrane after a deposition of silicon nitride on both sides.

FIG. 4 is a cross-sectional view illustrating the deposition of low-stress nitride ($Si_xN_y$) films 30 and 31 on both sides of the silicon substrate 10 resulting from the processing step shown in FIG. 3A. Either PECVD or LPCVD can be used for this step. The probes resulting from the completion of all steps described herein will include cantilevers made from the nitride film 31. With appropriate changes in processing, other materials compatible with silicon processing can be used instead of low-stress nitride, for instance stoichiometric nitride, polymers, metals, composites, or other semiconductor materials known to those skilled in the art. The thickness of this film is a function of the desired specifications of the probes, including the resonant frequency and spring constant. A critical part of this step is the careful cleaning of the silicon substrate 10 immediately prior to the nitride deposition. A thin layer of silicon dioxide may be formed during the industry-standard diffusion clean process, a wet chemical wafer cleaning. This layer can result in the silicon tips of the probes resulting from the completion of all steps described herein etching free from the nitride cantilevers in later oxide etch processing steps. To prevent this result, an oxide etch should be added to the end of the diffusion clean process so that the nitride can be deposited directly onto the silicon without the presence of a silicon dioxide layer between the two materials.

Figure 5A:
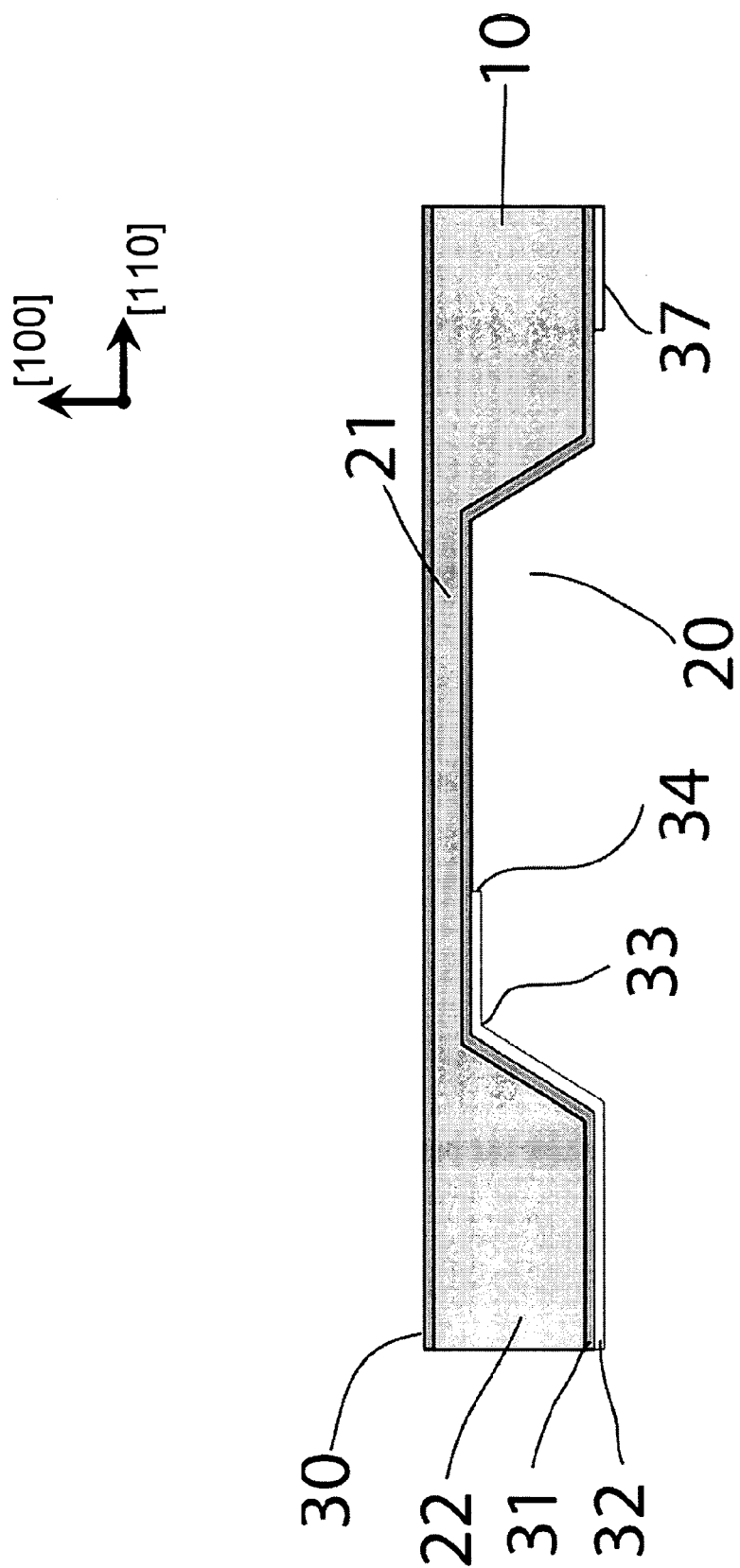
FIGS. 5A and 5B are, respectively, a cross-sectional view and bottom-side plan view showing an etch mask formed on the bottom side of the substrate via a shadow mask.
Figure 5B:
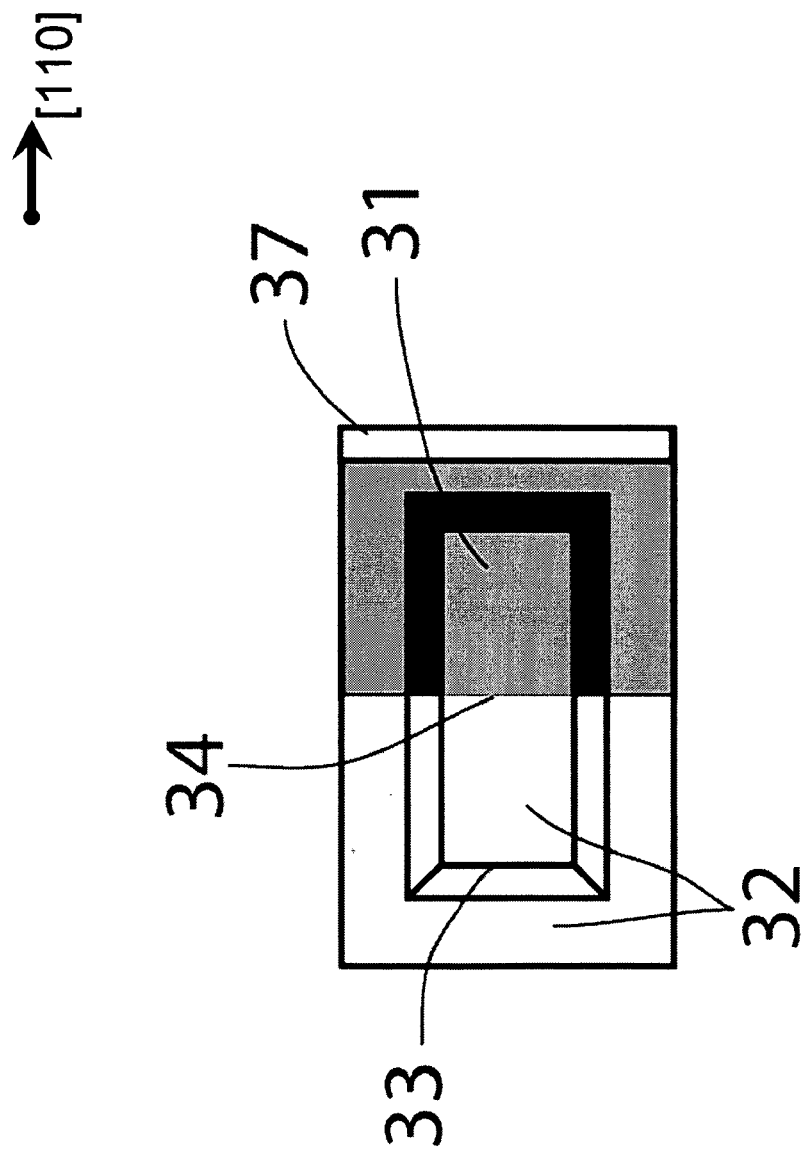

FIG. 5A shows a cross-sectional view of the process of depositing a mask layer 32 through a micromachined shadow mask (not shown) over a portion of the nitride film 31. The mask layer can be formed from metal, dielectric, polymer, or other materials known to those skilled in the art which will protect a nitride film during a RIE. Use of conventional lithography to define the mask layer would not be appropriate because the relatively deep rectangular pit 20 causes severe diffraction for a contact aligner, or focus limitations for projection lithography (stepper). Using e-beam lithography would also be inappropriate for mass production of these probes due to its extremely high cost. Completion of this step defines the length of the probes resulting from the completion of all steps described herein; the length will be the distance from point 33 to 34 on the mask layer 32. FIG. 5B shows a bottom-side plan view of the surface of the silicon substrate 10 on which the mask layer 32 has been deposited over a portion of the nitride film 31.

Figure 6A:
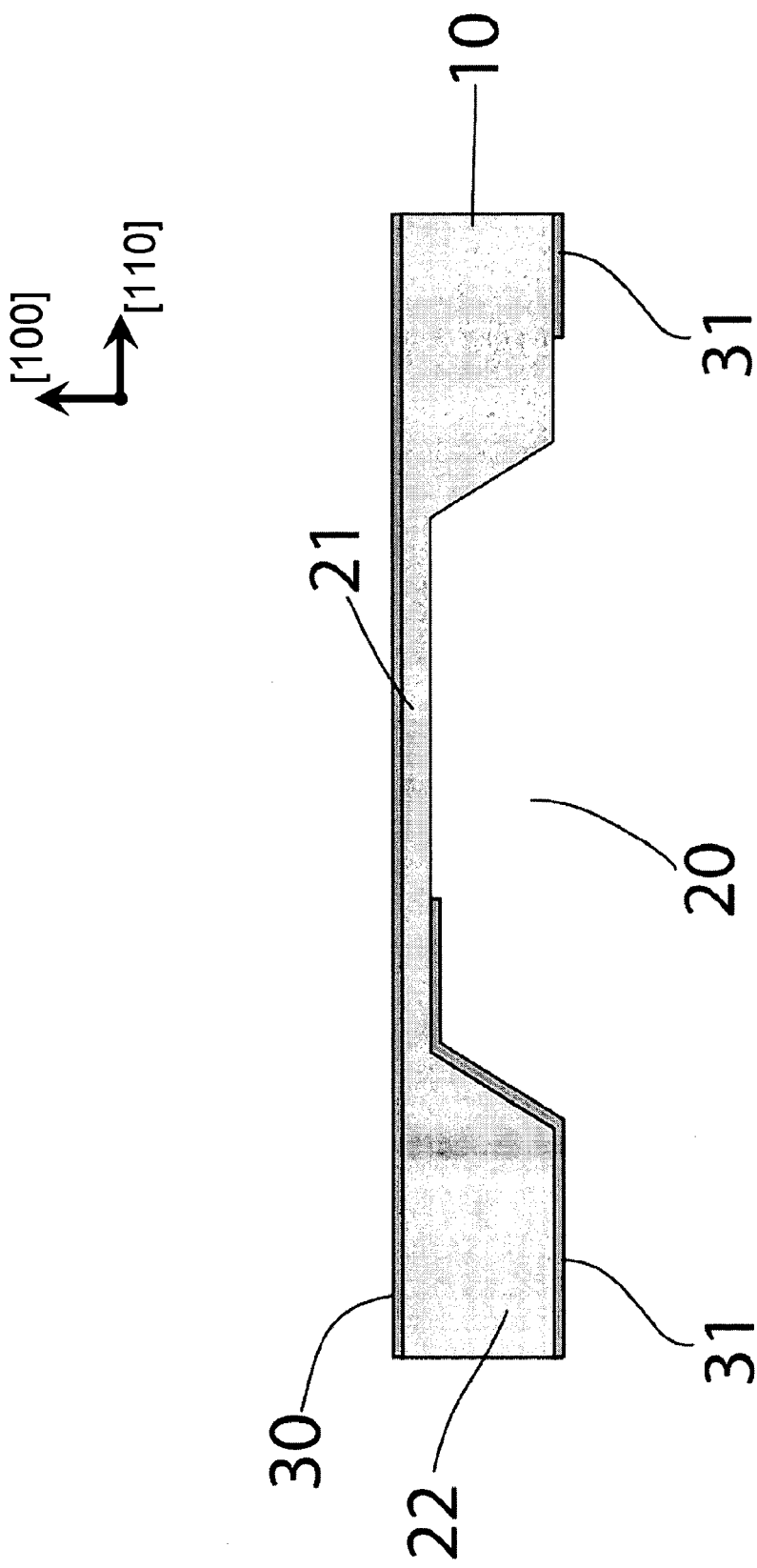
FIGS. 6A and 6B are, respectively, a cross-sectional view and bottom-side plan view showing the patterned silicon nitride on the bottom side of the substrate after the silicon nitride etch and mask removal.
Figure 6B:
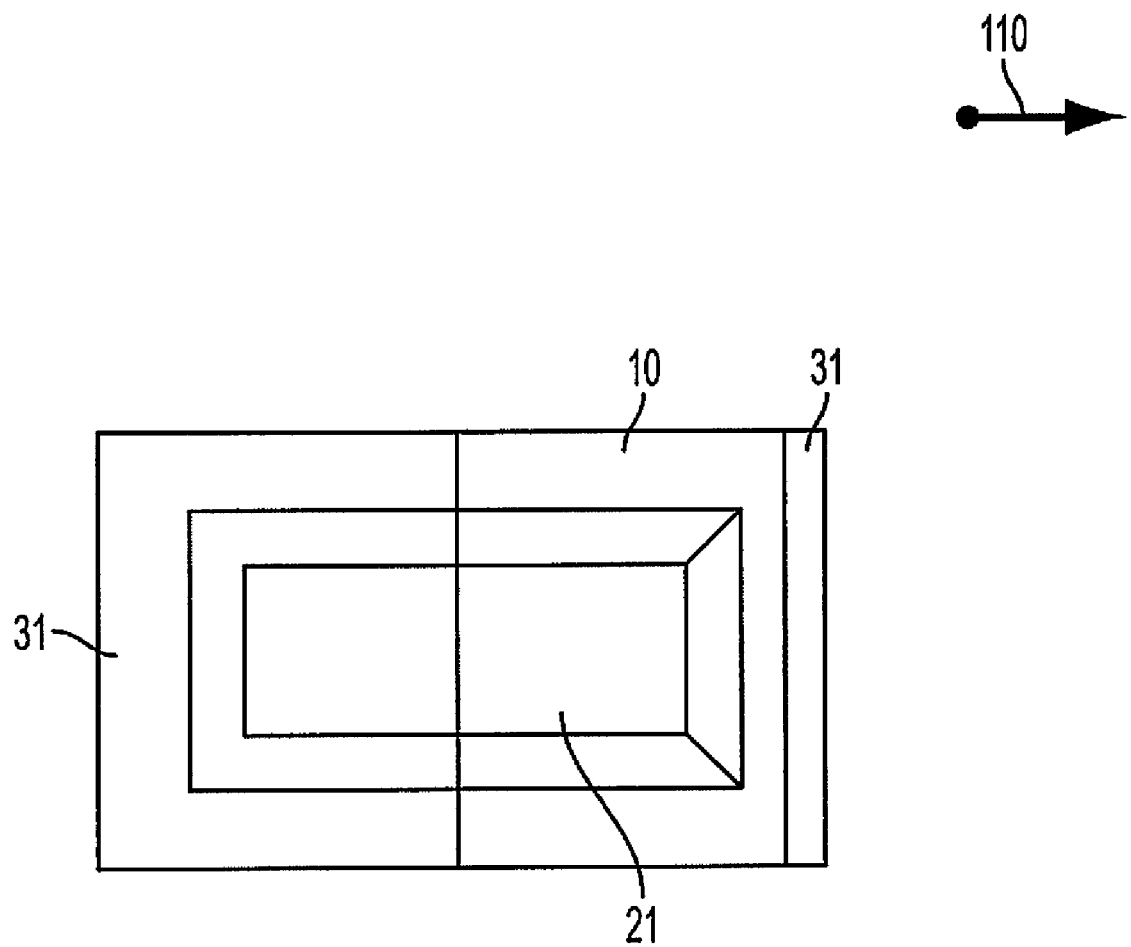

FIG. 6A shows a cross-sectional view of the RIE patterned nitride film 31 where the etch is stopped when the underlying silicon surface is reached. The RIE exposes a portion of the bottom surface of the silicon substrate 10, including portions of the membrane 21. FIG. 6B shows a bottom-side plan view of the surface of the silicon substrate 10 on which the unmasked nitride film 31 has been removed.

Figure 7A:
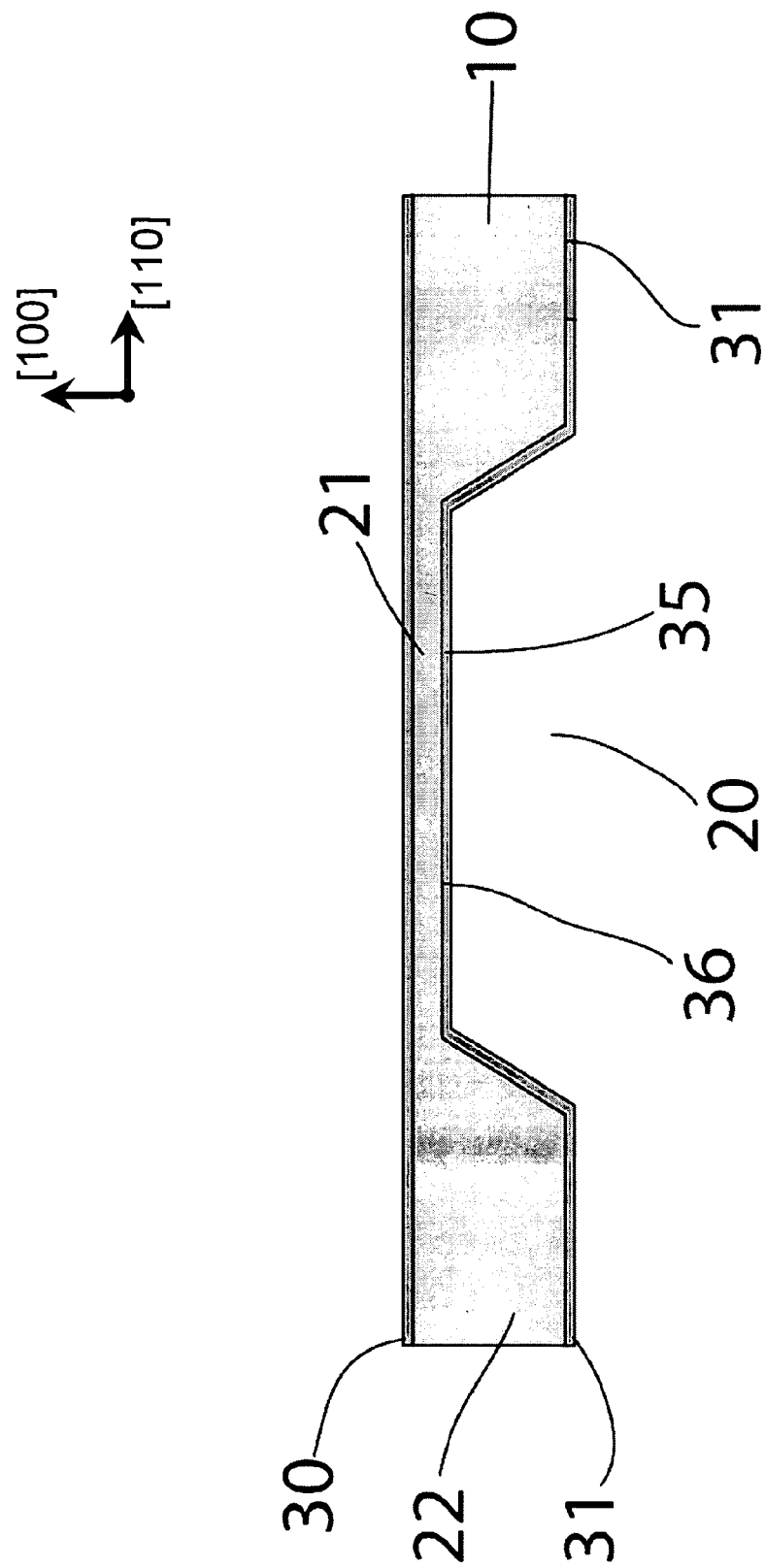
FIGS. 7A and 7B are, respectively, a cross-sectional view and bottom-side plan view showing the growth of silicon dioxide on the exposed bottom-side of the silicon substrate.
Figure 7B:
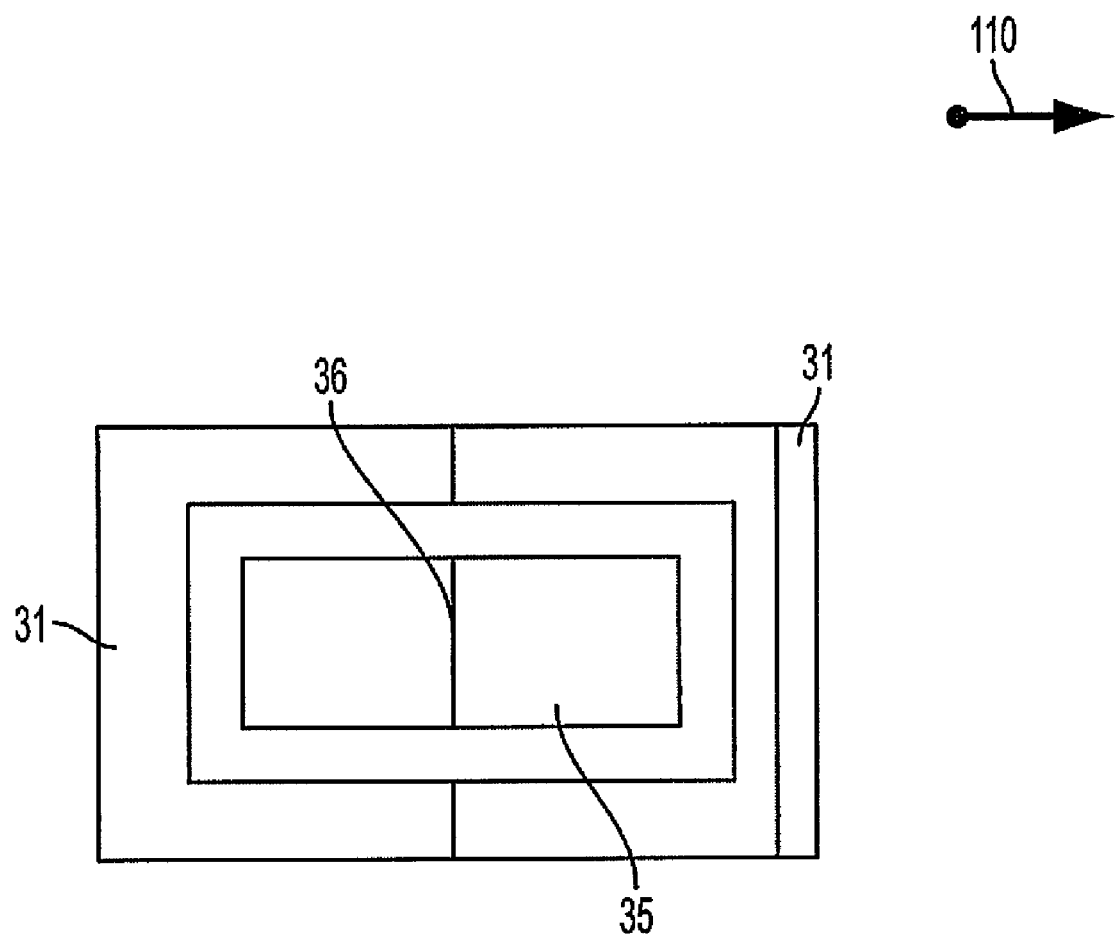

FIG. 7A shows a cross-sectional view of the silicon substrate 10 with a layer of oxide 35 grown on the exposed portion of the bottom surface. The nitride films 30 and 31 have prevented growth of oxide under and on the areas they cover. The nitride-oxide intersection 36 marks what will be the end of the nitride cantilever and the beginning of the sacrificial oxide cantilever extension. FIG. 7B shows a bottom-side plan view of the silicon substrate 10 on which a layer of oxide 35 has been grown.

Figure 8A:
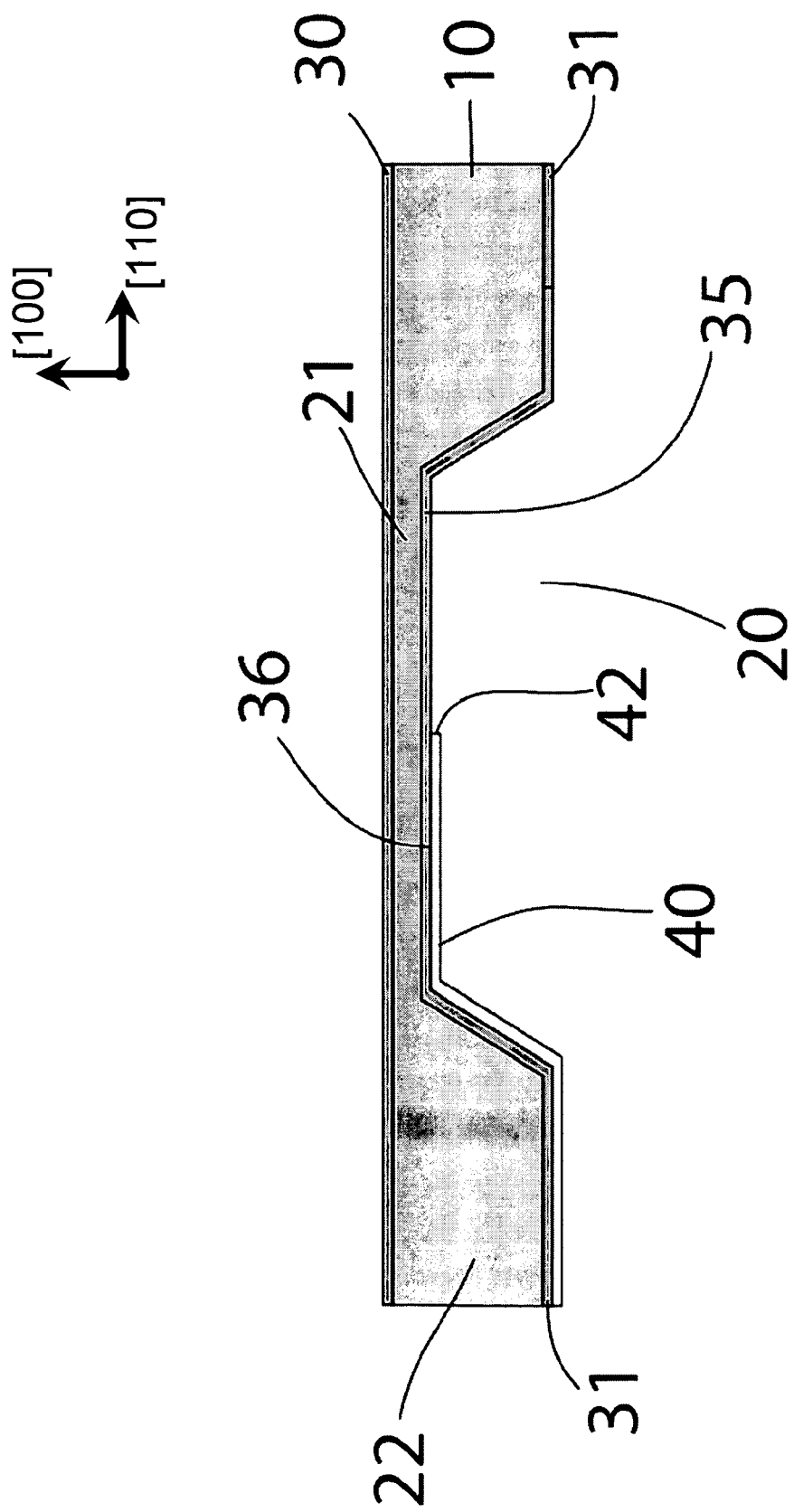
FIGS. 8A and 8B are, respectively, a cross-sectional view and bottom-side plan view showing a cantilever etch mask formed on the bottom side of the substrate via a shadow mask.
Figure 8B:
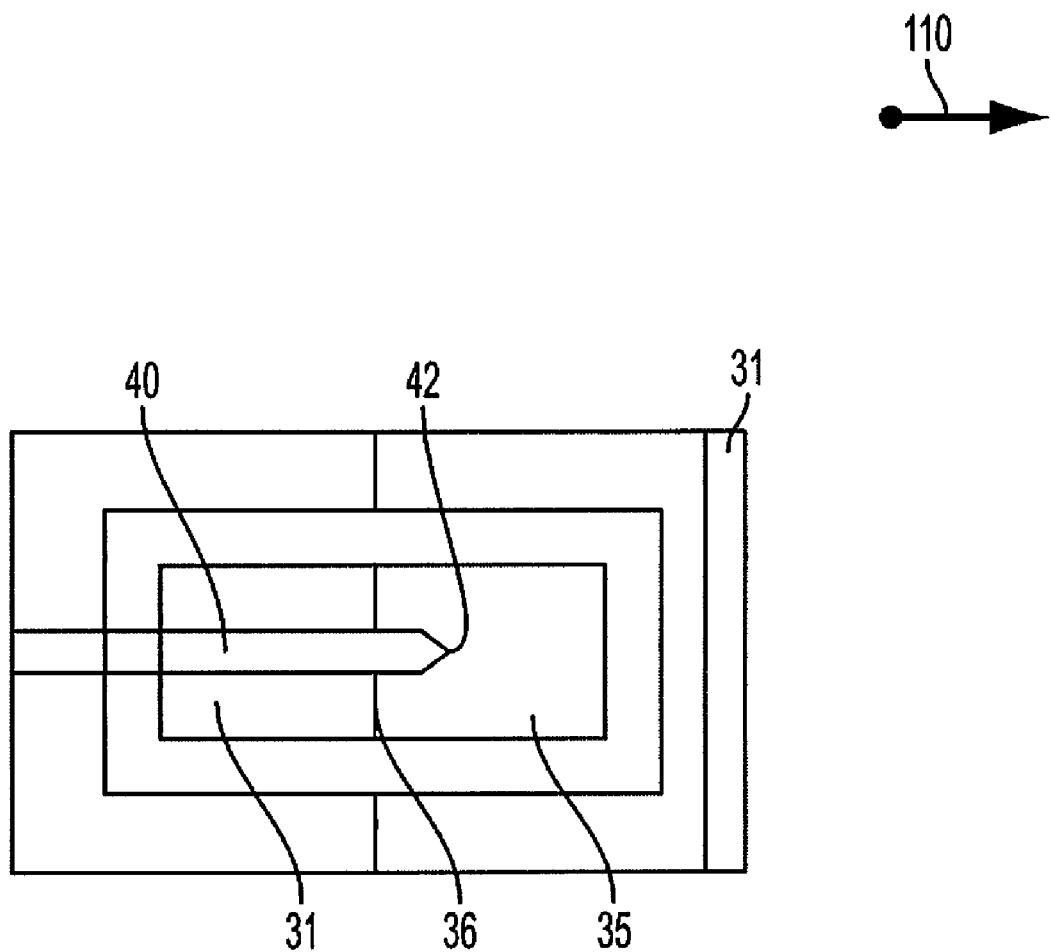

FIG. 8A shows a cross-sectional view of the process of depositing a cantilever mask layer 40 through a micromachined shadow mask (not shown) over a portion of the nitride film 31 and oxide film 35. Such mask layers have been discussed in connection with the process depicted in FIG. 5A. The mask layer 40 results in the patterning of the probes to result from completion of all steps described herein. FIG. 8B, a bottom-side plan view of the silicon substrate 10, shows the cantilever mask layer 40 pointing in the [110] crystal plane direction. The end 42 of the cantilever mask layer 40 extending over the oxide layer 35 is designed to be undercut etched during the anisotropic silicon wet etching depicted in FIG. 10A while exposing desired sidewall etch planes. The cantilever end can be square, but can also be triangular with two lines along crystallographic directions, for instance the [410] direction or other desired directions, to shorten the undercut etch time.

Figure 9A:
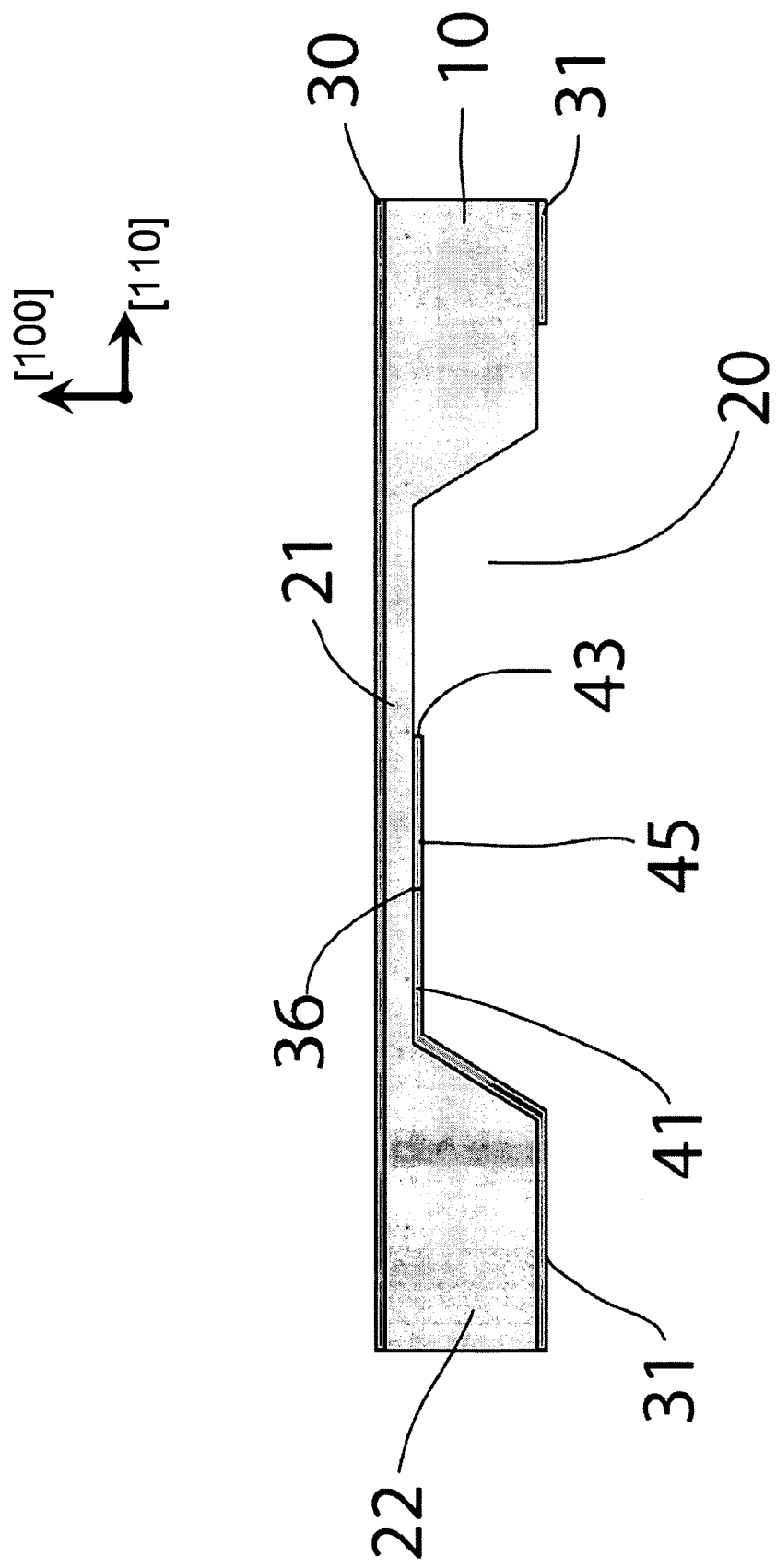
FIGS. 9A and 9B are, respectively, a cross-sectional view and bottom-side plan view of the substrate showing the patterned silicon nitride cantilever with a sacrificial silicon dioxide extension.
Figure 9B:
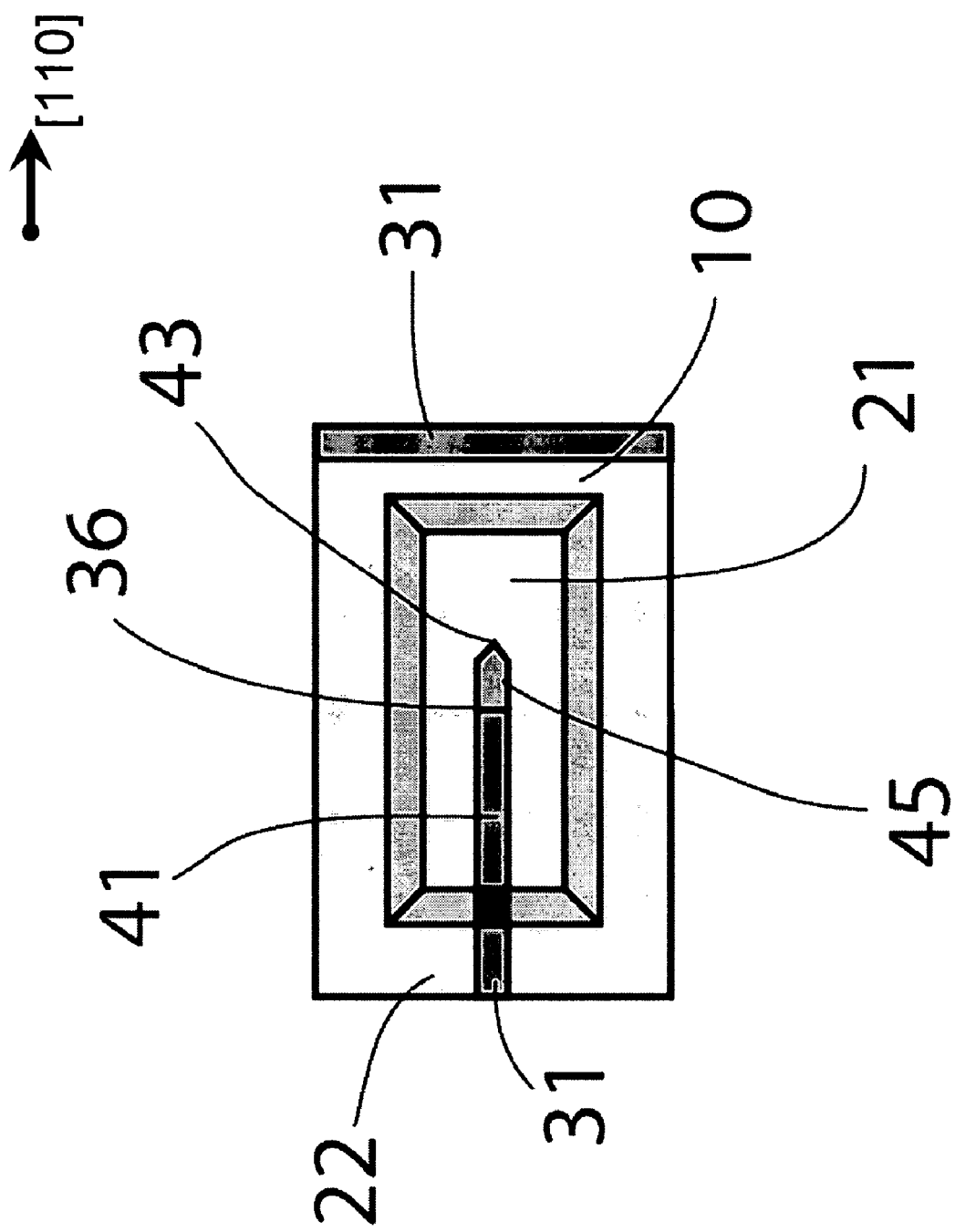

FIG. 9A shows a cross-sectional view of the transferred cantilever pattern into the nitride and oxide films, respectively 31 and 35. The nitride pattern 41 results from removing all the nitride film 31 excepting the patterned portion 41 with a RIE. The oxide pattern 45 results from removing all the oxide film 35 excepting the patterned portion 45 with dilute HF or BOE solution. The nitride pattern 41 will become the cantilever of the probes resulting from completion of all steps described herein. FIG. 9B, a bottom-side plan view of the silicon substrate 10, shows the patterning more clearly.

Figure 10A:
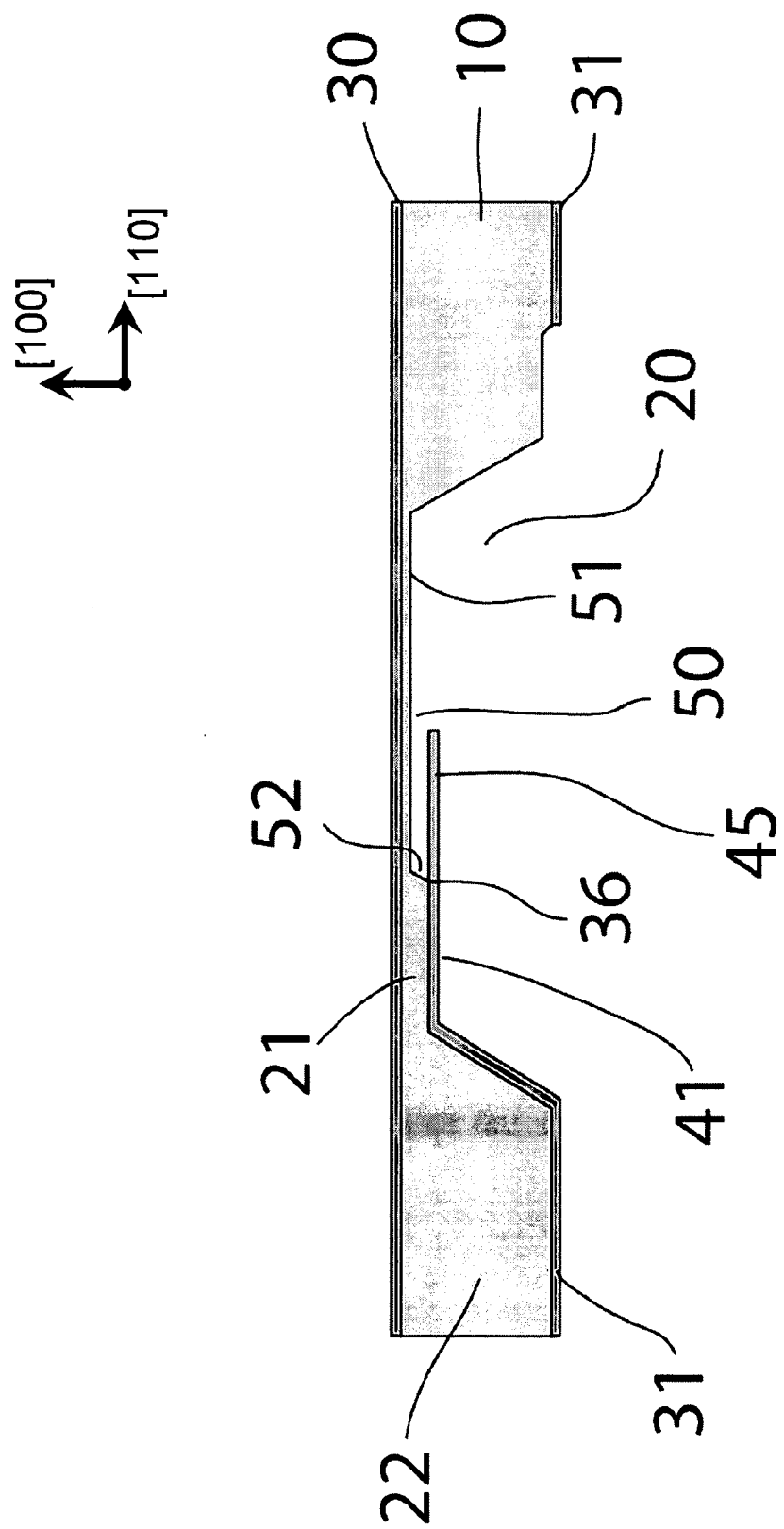
FIGS. 10A and 10B are, respectively, a cross-sectional view and bottom-side plan view of the substrate showing the anisotropic etch of the bottom-side silicon.
Figure 10B:
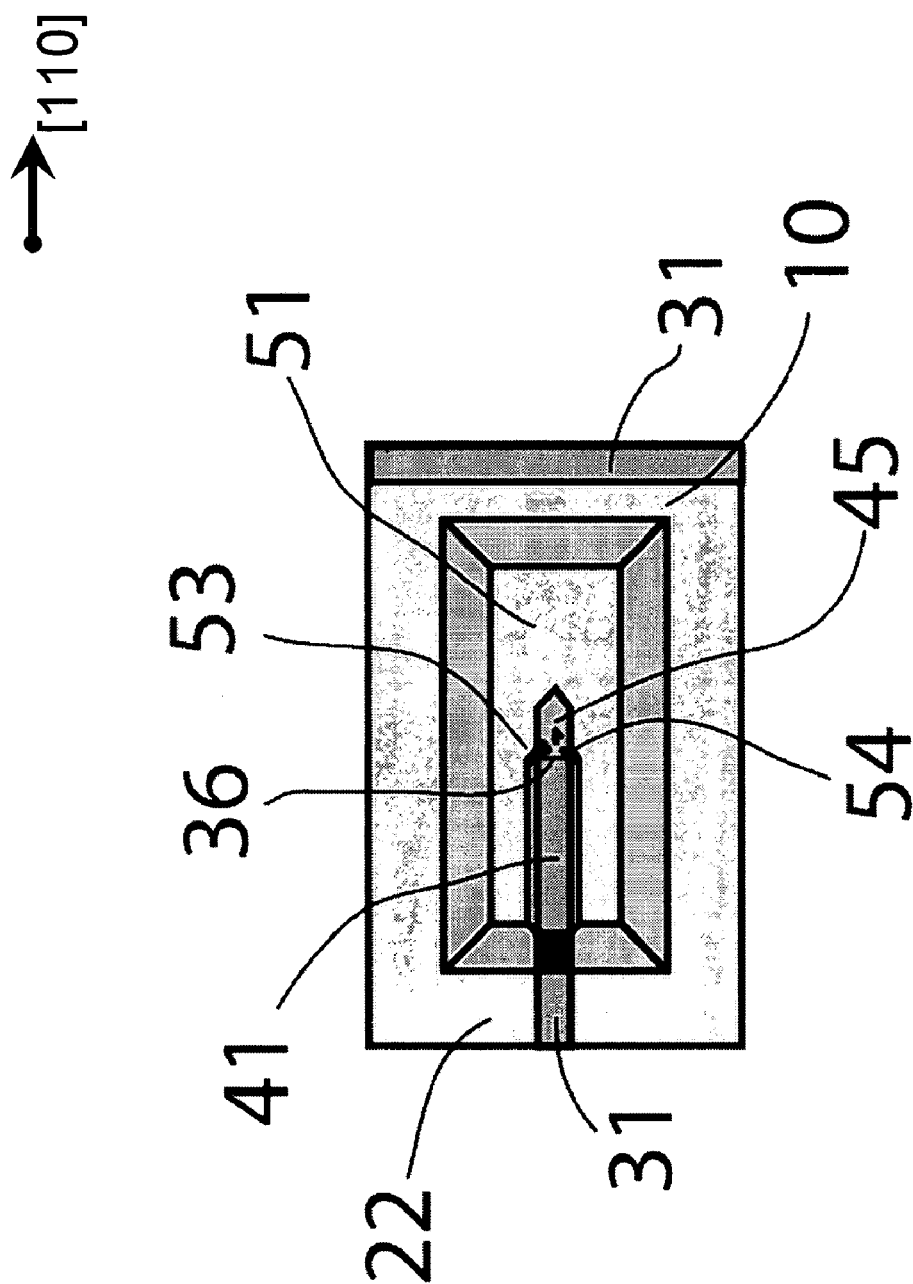

FIG. 10A shows a cross-sectional view of the silicon substrate 10 after a wet anisotropic silicon etch. During the etch, two main etch planes {411} slowly undercut etch the silicon underlying the oxide pattern 45. The etch is progressed until the rectilinear intersection 52 of these two undercutting {411} etch planes reaches (or passes depending on the application) the junction 36 of the nitride pattern 41 and the oxide pattern 45. The two etch planes will later form two exterior facets of the tetrahedral silicon tip of the probes resulting from the completion of all steps described herein. The etch creates an etch pit 50, further thinning the unmasked part of the silicon membrane 21, with the bottom of the pit being the thinner silicon membrane 51. FIG. 10B, a bottom-side plan view of the silicon substrate 10, shows the result of the anisotropic silicon etch more clearly.

Figure 11:
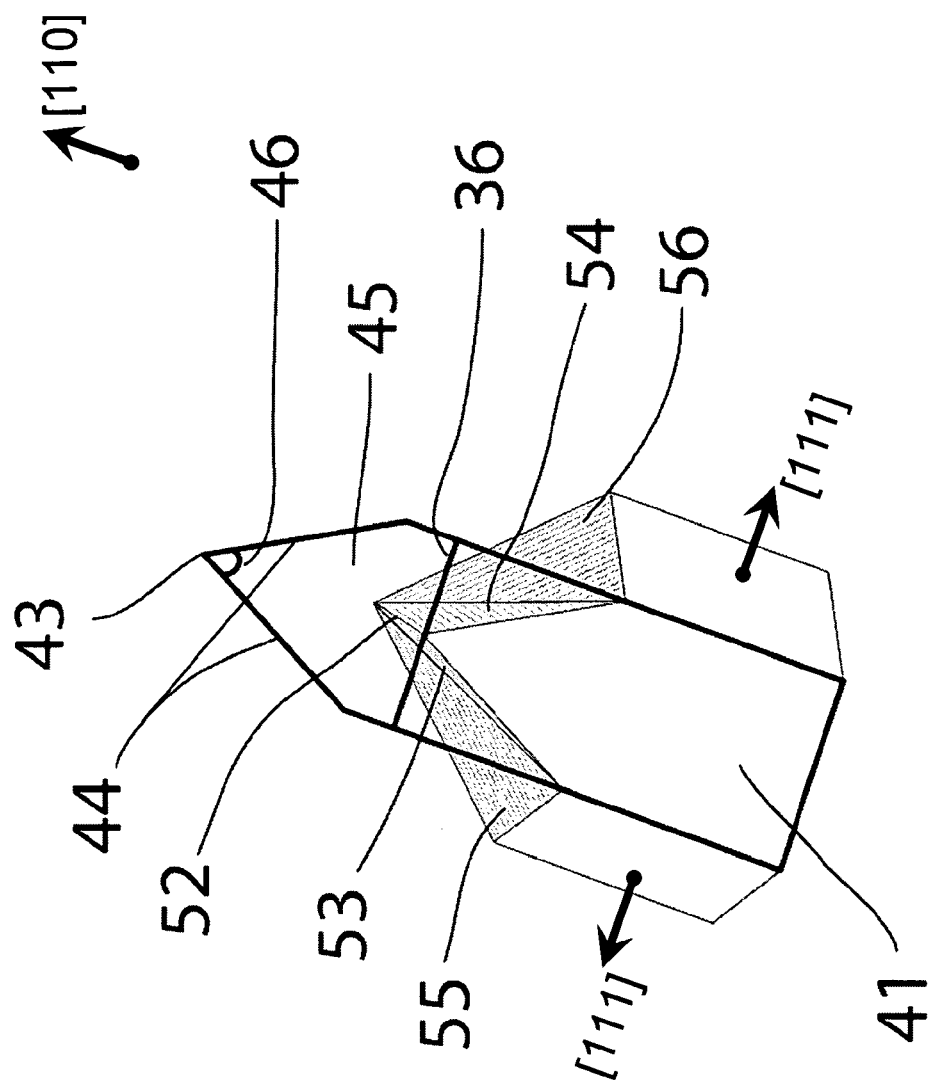
FIG. 11 is an enlarged, bottom-side perspective view of the anisotropic silicon etch with the undercut just past the end of the silicon nitride cantilever.

FIG. 11 shows an enlarged perspective view from the bottom direction of the result of the anisotropic silicon etch. The foreground of FIG. 11 shows the nitride pattern 41 and the oxide pattern 45 meeting at junction 36. The end 43 of the oxide pattern 45 is formed into an arrow point where the sides of the arrow 44 align with the [410] silicon crystal directions. The rectilinear intersection 52 of silicon surfaces 53 and 54, which are {411} crystal planes, forms an angle of approximately 74° with respect to the [110] silicon crystal direction. The arrow point geometry of the oxide pattern 45 is designed to force the {411} crystal planes 53 and 54 to reveal themselves sooner in the undercut etch when compared to the result with a square-end geometry. The edges 44 of the oxide pattern 45 can also be aligned with other crystal directions, like the [310] or even non-crystal plane directions, in order to optimize the formation of the surfaces 53 and 54 during undercut etching. However, the final etch profiles of surfaces 53 and 54 will still select the {411} crystal plane orientation. In practice, surfaces 55 and 56 are not specific crystal planes. Instead they reveal themselves as multitudinous irregular etch planes. For convenience they are represented here as single planes.

Figure 12:
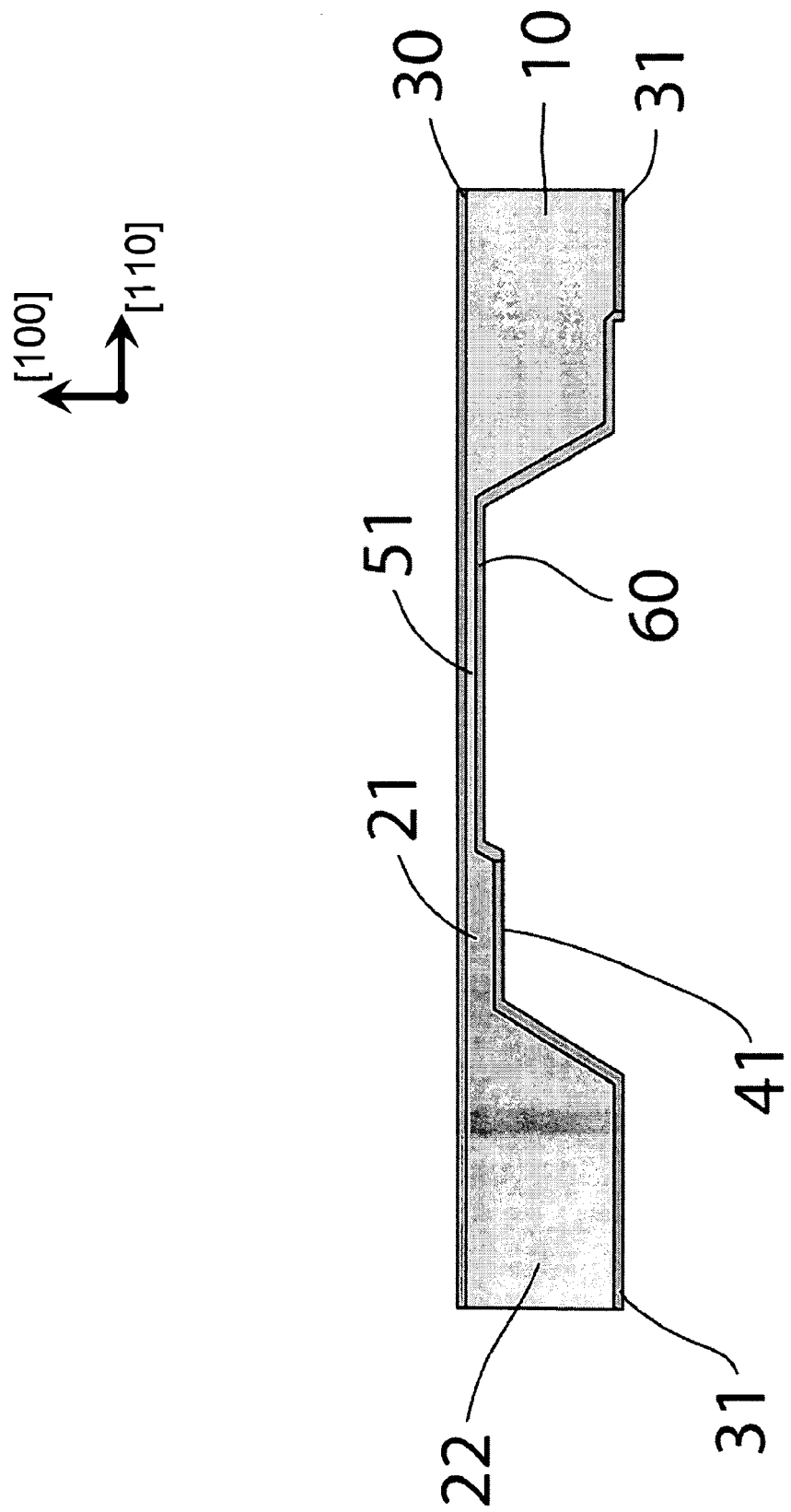
FIG. 12 is a cross-sectional view after the removal of the sacrificial oxide cantilever extension and subsequent re-growth of silicon dioxide on the exposed silicon surfaces on the bottom-side of the substrate.

FIG. 12 shows a cross-sectional view of the silicon substrate 10 after the next two steps, an oxide etch step followed by an oxide growth step. In the first step, the oxide pattern 45 is removed with HF or BOE solution. In the second step, an oxide film 60 is grown on all exposed silicon surfaces on the bottom-side of the silicon substrate 10. The result of this second step is a complete bottom-side etch mask formed from the two sections of nitride film, 31 and 41, and the section of oxide film 60.

Figure 13A:
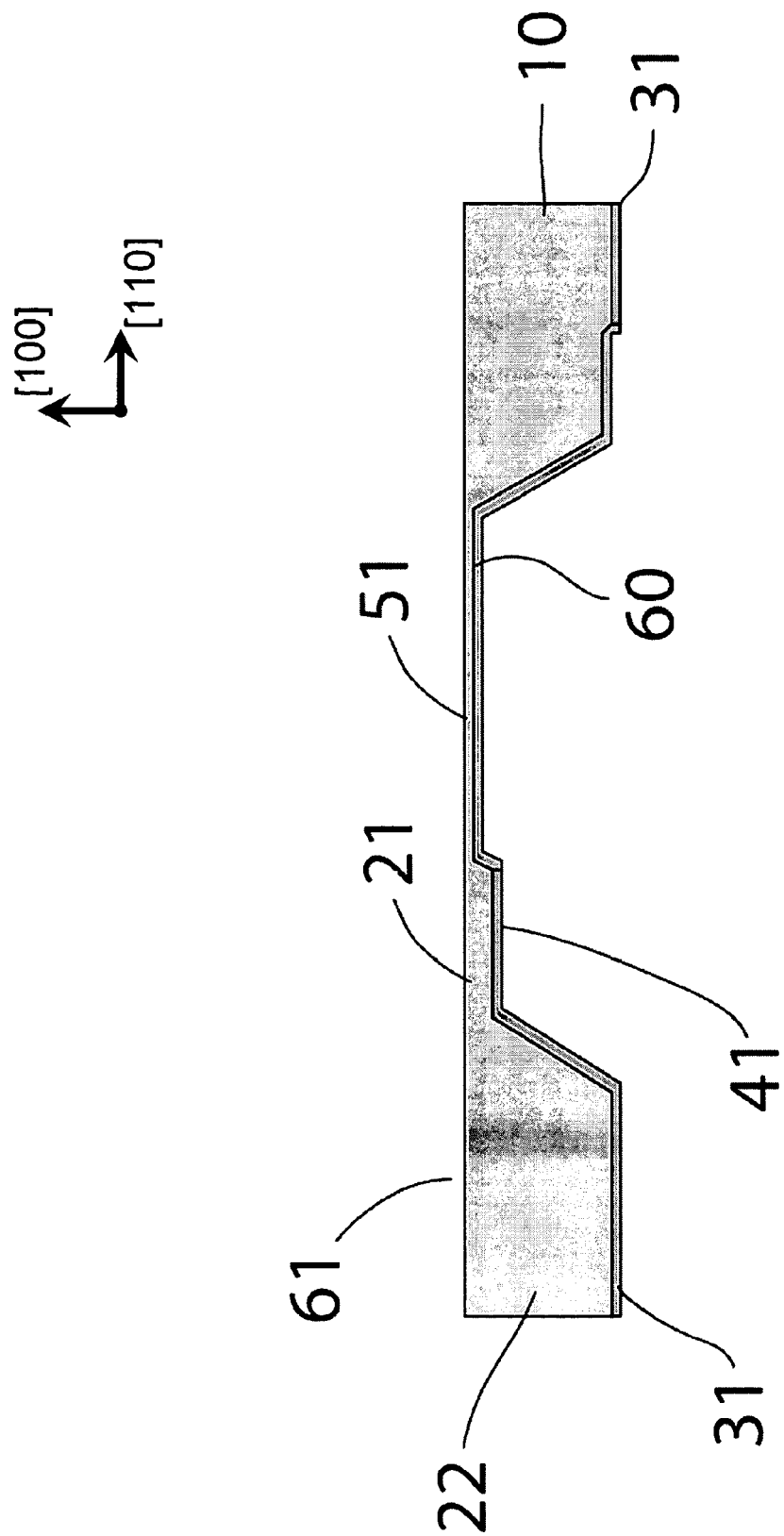
FIG. 13A is a cross-sectional view of the substrate after the removal of the top-side silicon nitride layer.
Figure 13B:
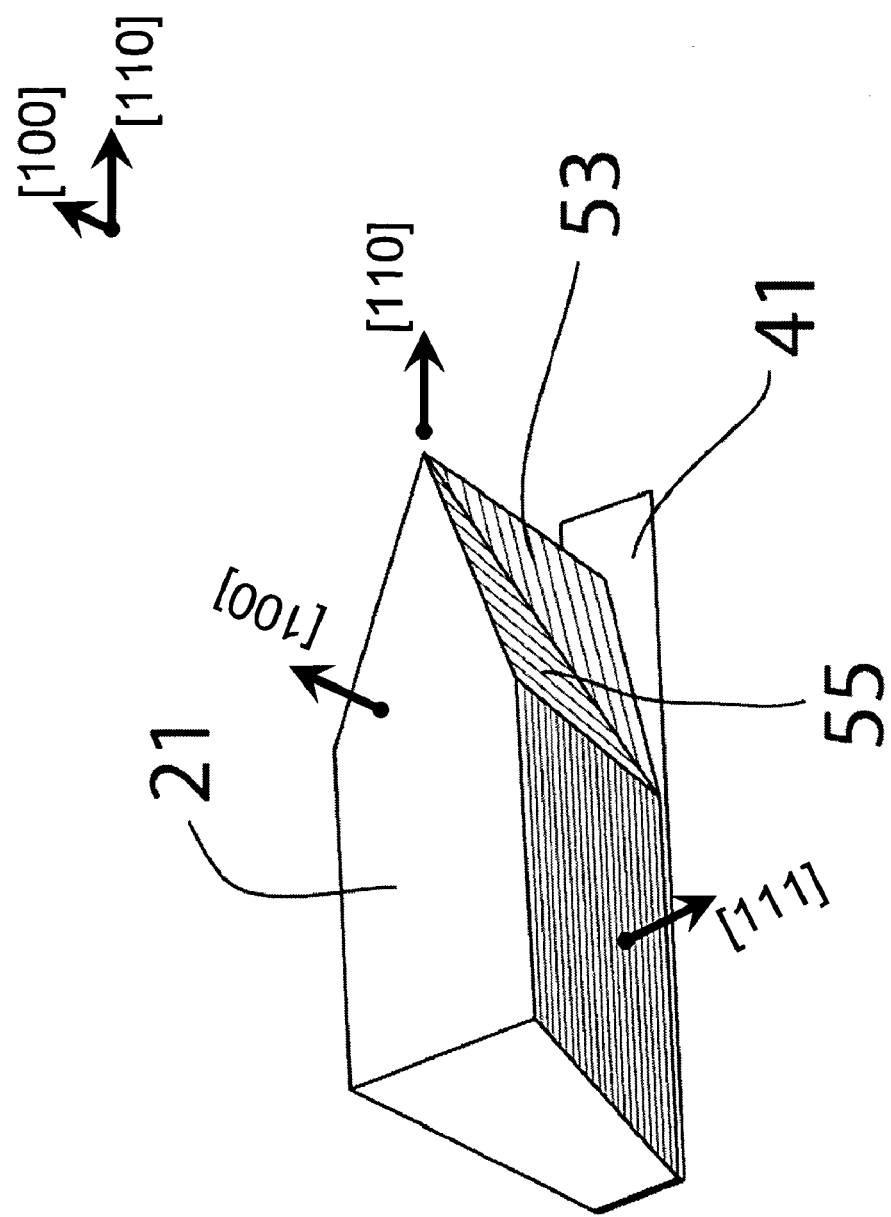
FIG. 13B is an enlarged, top-side perspective view of the substrate after the removal of the sacrificial oxide cantilever extension with an obstructing thin silicon membrane removed for illustrative purposes.

FIG. 13A shows a cross-sectional view of the result of removing the top-side nitride film 30 by a RIE, exposing the top surface of the silicon substrate 10. FIG. 13B shows an enlarged perspective view from the top direction after the step depicted in FIG. 13A. Unlike the depiction in FIG. 11, here the nitride pattern 41 that will become the cantilever of the probes resulting from completion of all steps described herein is in the background rather than the foreground. The silicon surface in the foreground 21 is shown with the silicon membrane 51 stripped away only for illustrative purposes. The growth of the oxide film depicted in FIG. 12 extends to the (111) crystal plane and the surfaces 53 and 55, together with the other (111) crystal plane (not shown) and the surfaces 54 and 56 (also not shown). This film serves as an etch mask in connection with the formation of a tetrahedral silicon tip during the wet anisotropic silicon etch depicted in FIG. 14A.

Figure 14A:
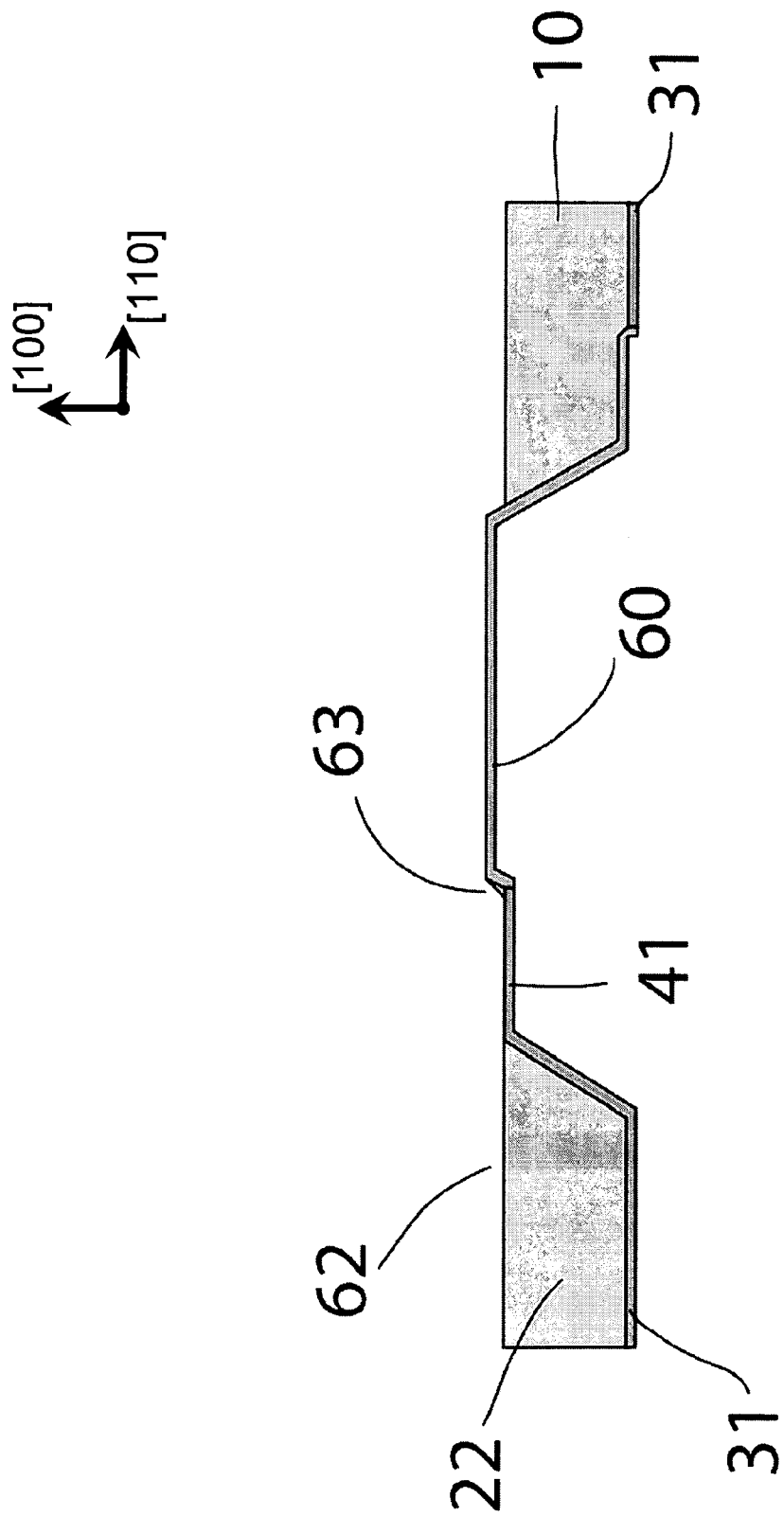
FIGS. 14A and 14B are, respectively, a cross-sectional view and an enlarged cross-sectional view of the substrate after the silicon membrane is completely removed in an anisotropic etch, leaving only a silicon tetrahedral tip attached to the bottom-side nitride cantilever and bottom-side oxide.
Figure 14B:
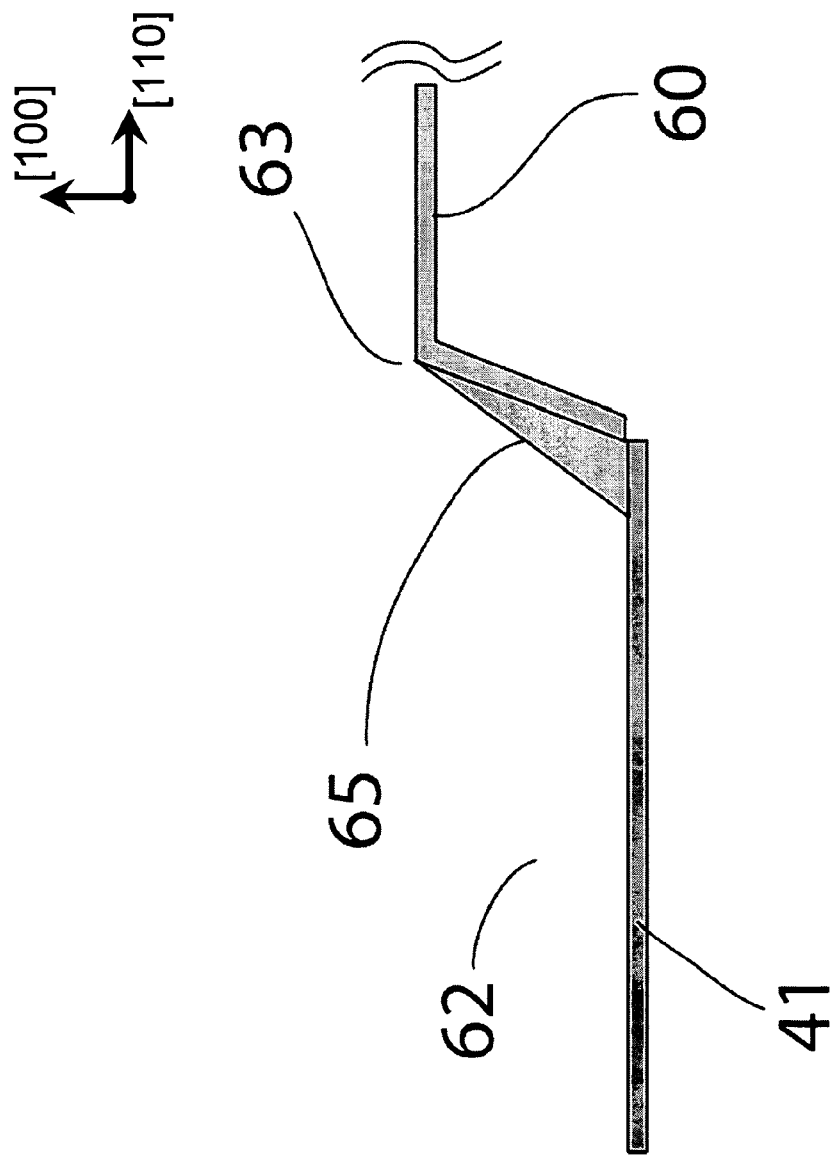

FIG. 14A shows a cross-sectional view of the process of forming a silicon tip 63 on the nitride pattern 41 by etching the exposed top-side surface of the silicon substrate 10 with a wet anisotropic silicon etch. The etch is allowed to proceed down to the top of the nitride pattern 41, completely removing the thin silicon membranes 21 and 51 except for a small silicon tip 63, exposing the nitride pattern 41 and the oxide film 60. The handle 22 of the probes resulting from completion of all steps described herein is now separated from the remainder of the silicon substrate 10. FIG. 14B shows a zoomed-in cross-sectional view of the step depicted in FIG. 14A. The handle 22 of the probe is not shown. Surface 65 of the tip of the probe is formed during the wet silicon etch and is a (111) crystal plane. The oxide layer 60 will be removed with diluted HF or BOE solution to release the tip 63 and the nitride pattern 41, which is now the cantilever. The bond between the tip 63 and the cantilever 41 will hold during the etch of oxide film 60 because there is no intermediate oxide layer between the nitride cantilever 41 and the silicon tip 63 as discussed in connection with the process depicted in FIG. 4.

Figure 15:
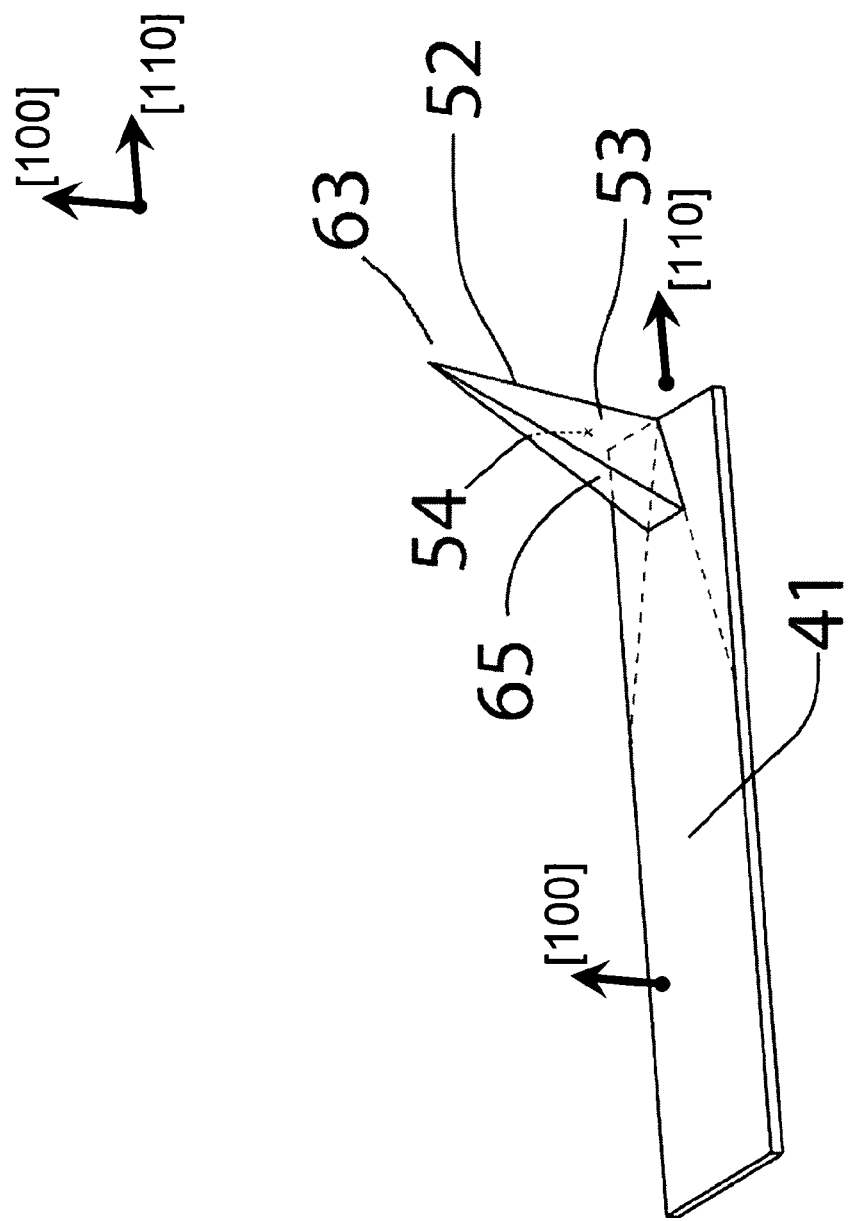
FIG. 15 is an enlarged perspective view of the tetrahedral silicon tip and nitride cantilever after the removal of the bottom-side oxide.

FIG. 15 shows an enlarged perspective view of the silicon nitride cantilever 41 with a tetrahedral three-sided silicon tip 63. The surface 65 is a (111) crystal plane, the slowest etch plane in wet anisotropic silicon etch. The surfaces 53 and 54 are {411} crystal planes whose rectilinear intersection 52 forms an angle of approximately 74° with the nitride cantilever 41.

Figure 16:
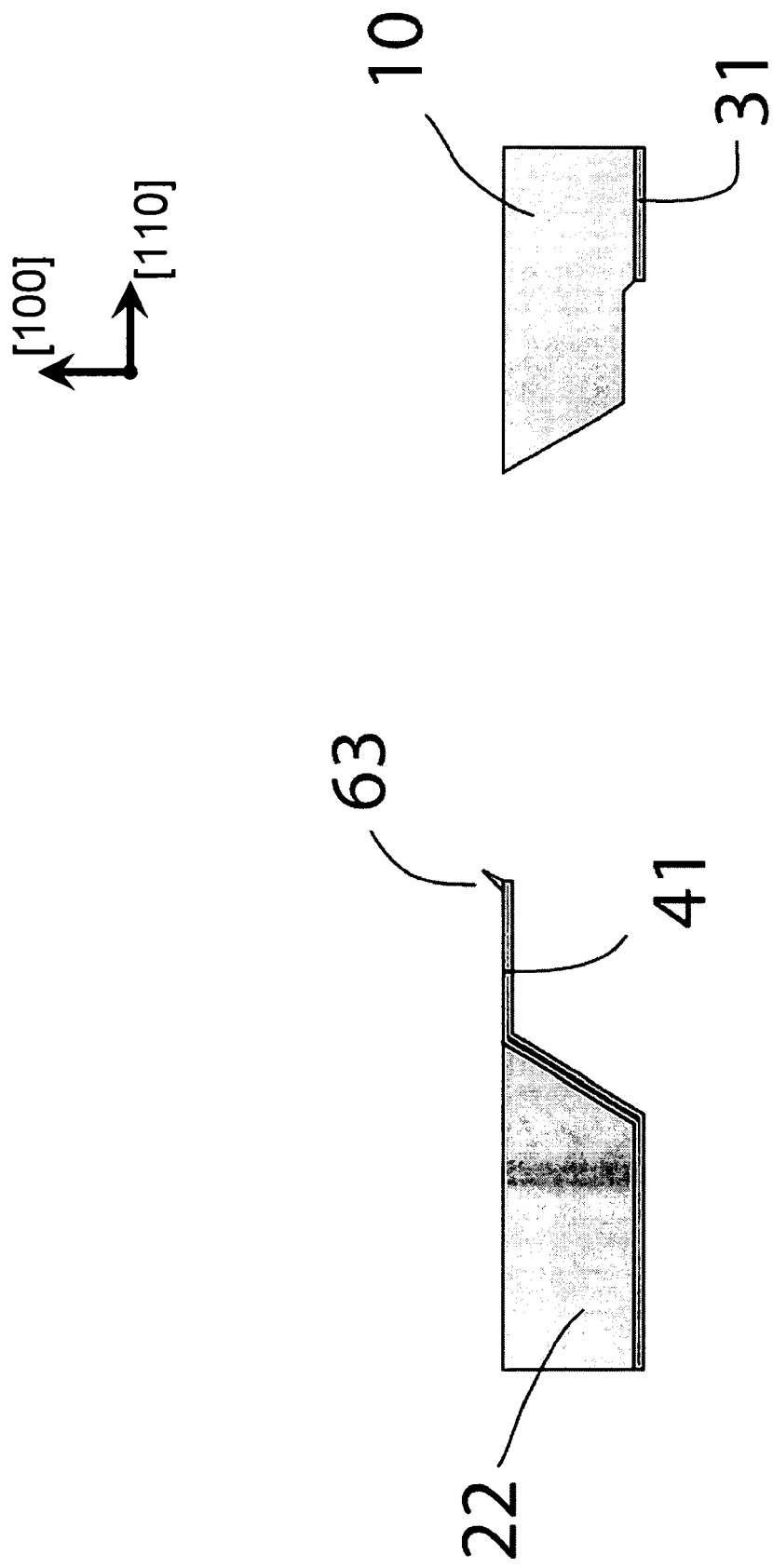
FIG. 16 is a cross-sectional view of the silicon handle, the nitride cantilever, and silicon tip after the removal of the bottom-side oxide.
Figure 108A:
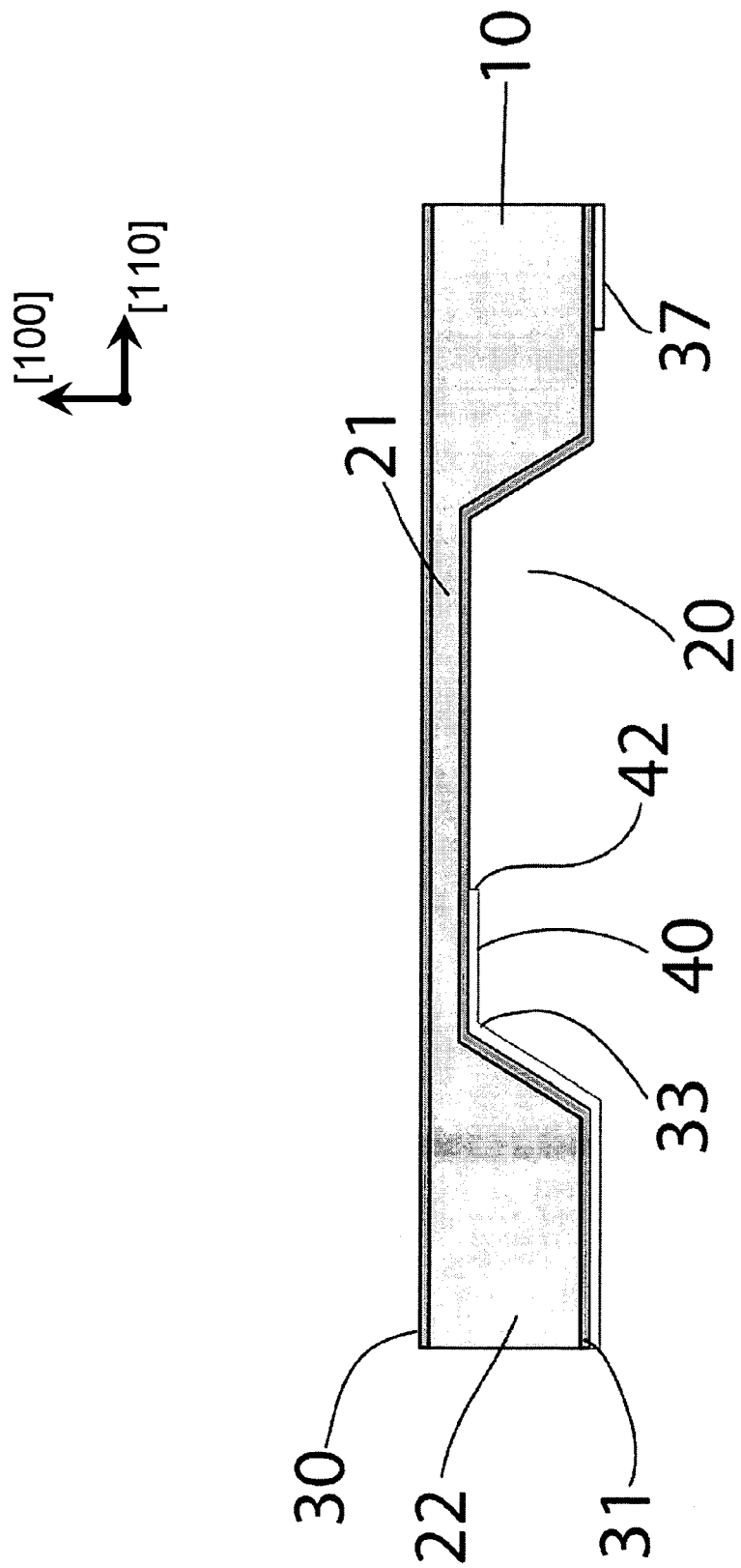
FIGS. 108A and 108B are, respectively, a cross-sectional view and a bottom-side plan view showing a cantilever etch mask formed on the bottom-side of the substrate via a shadow mask, which is part of the second embodiment of the present invention.
Figure 108B:
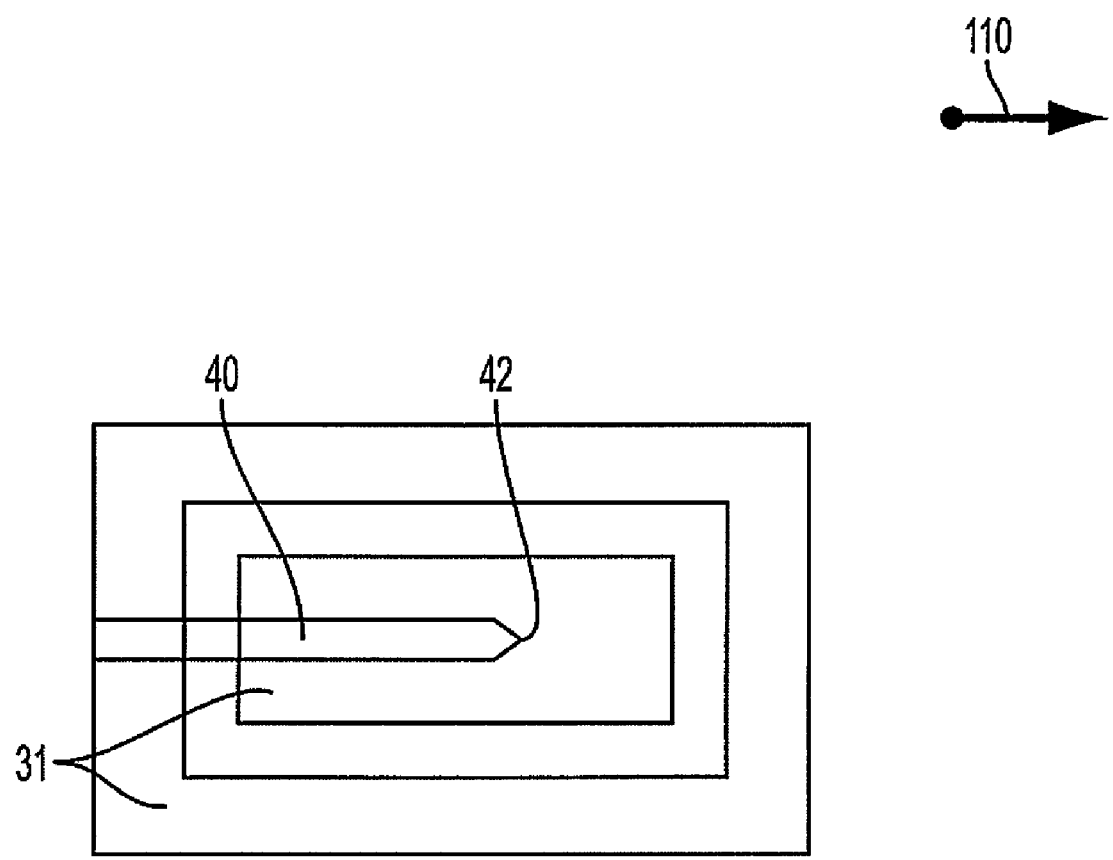
Figure 109A:
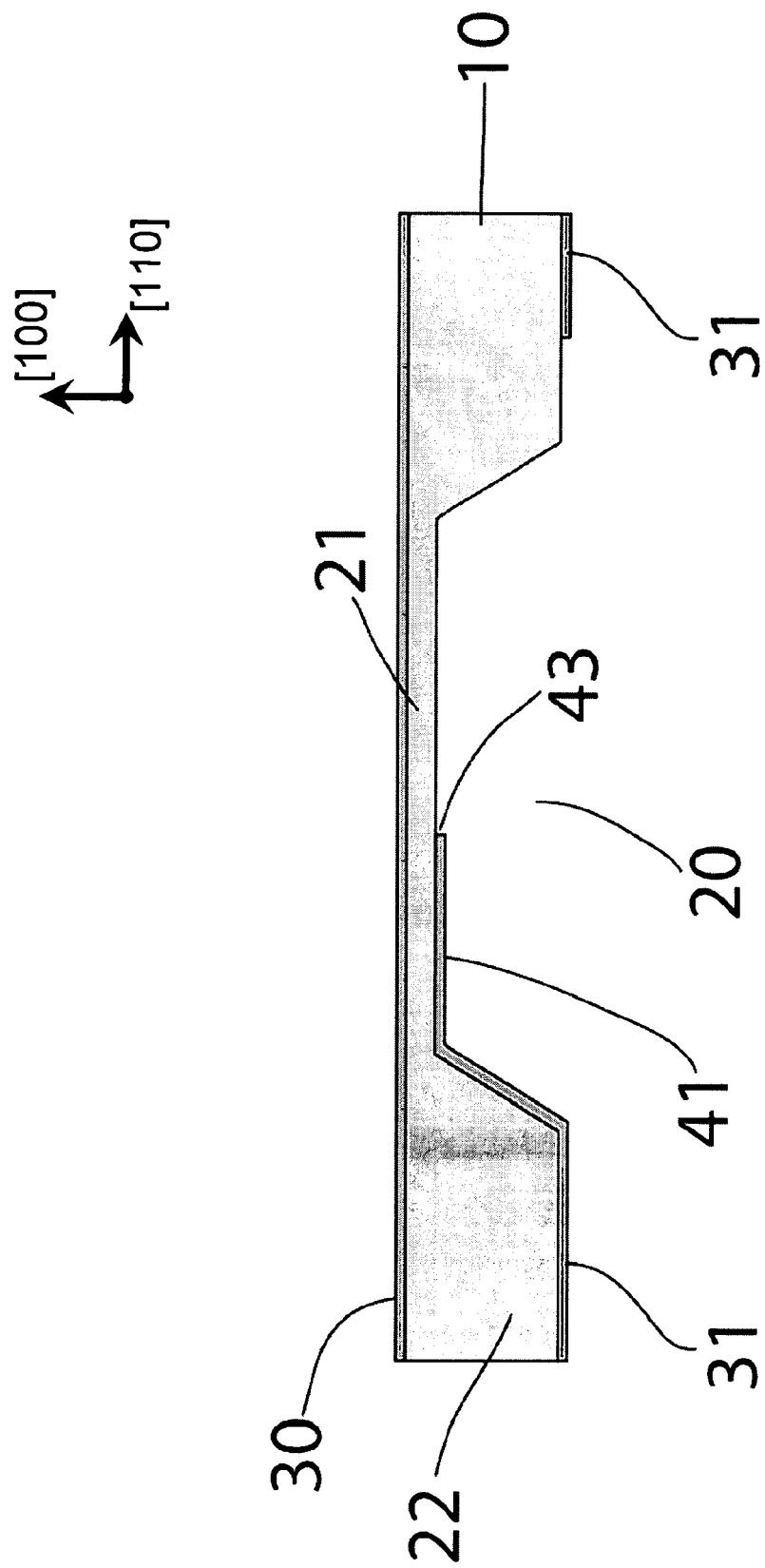
FIGS. 109A and 109B are, respectively, a cross-sectional view and a bottom-side plan view of the substrate showing the patterned silicon nitride cantilever.
Figure 109B:
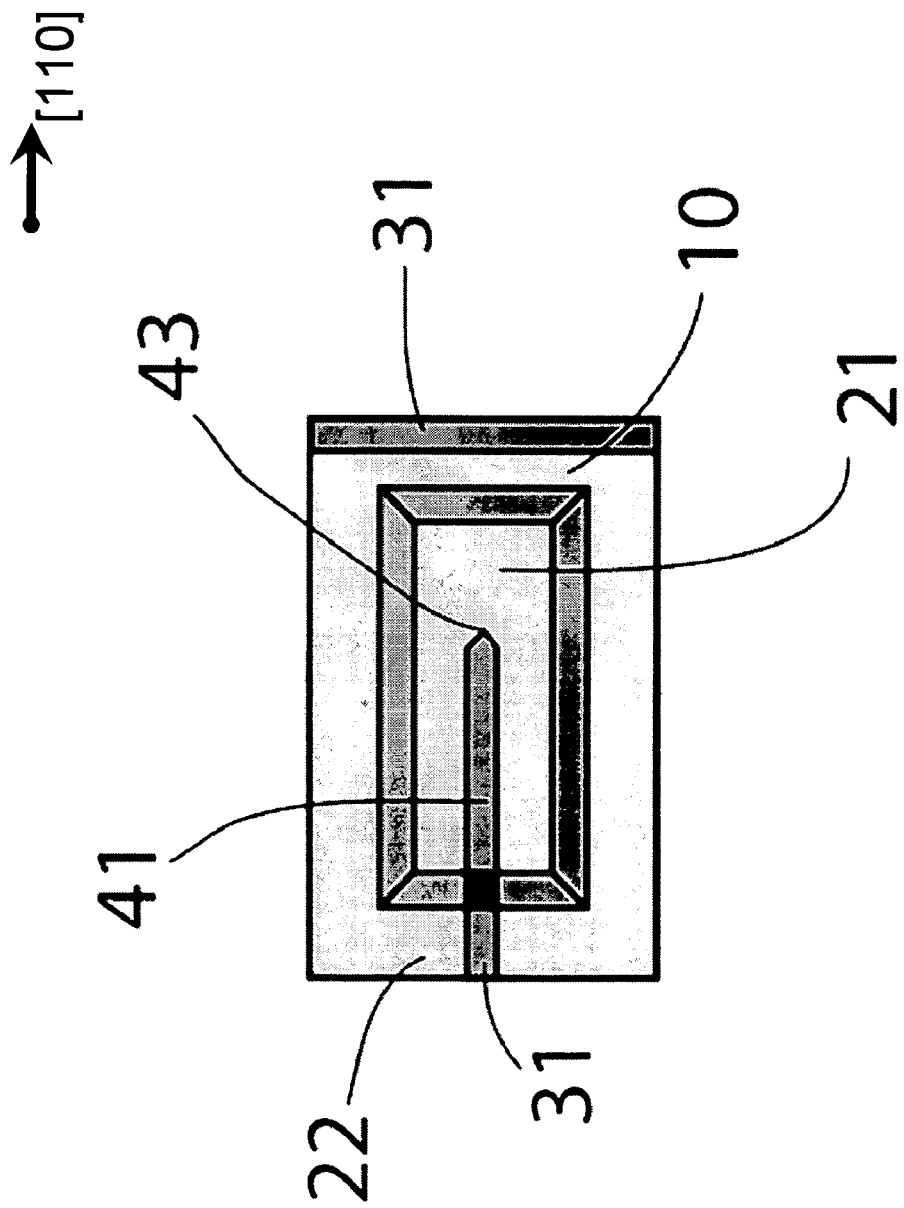
Figure 110A:
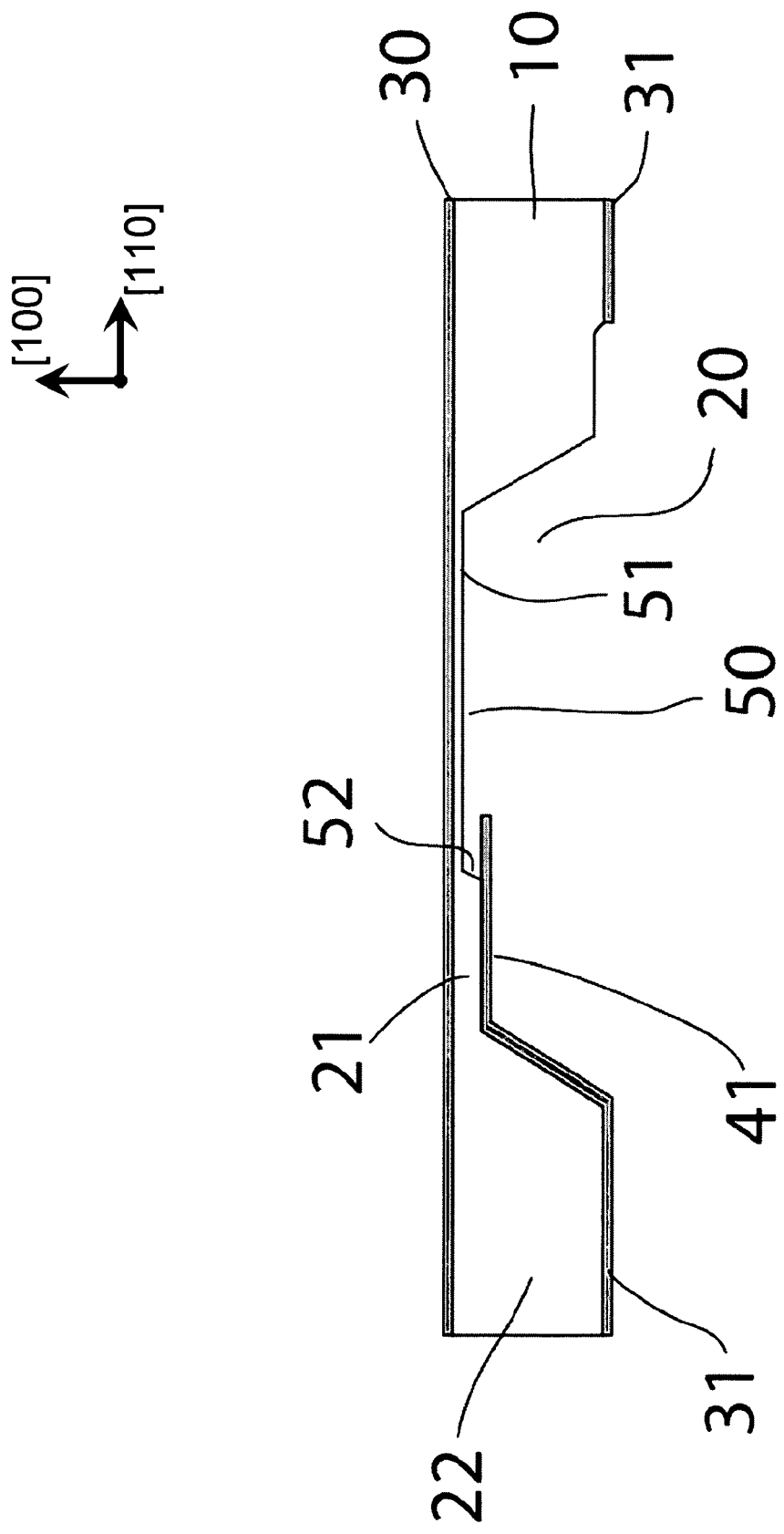
FIGS. 110A and 110B are, respectively, a cross-sectional view and a bottom-side plan view of the substrate showing the anisotropic etch of the bottom-side silicon.
Figure 110B:
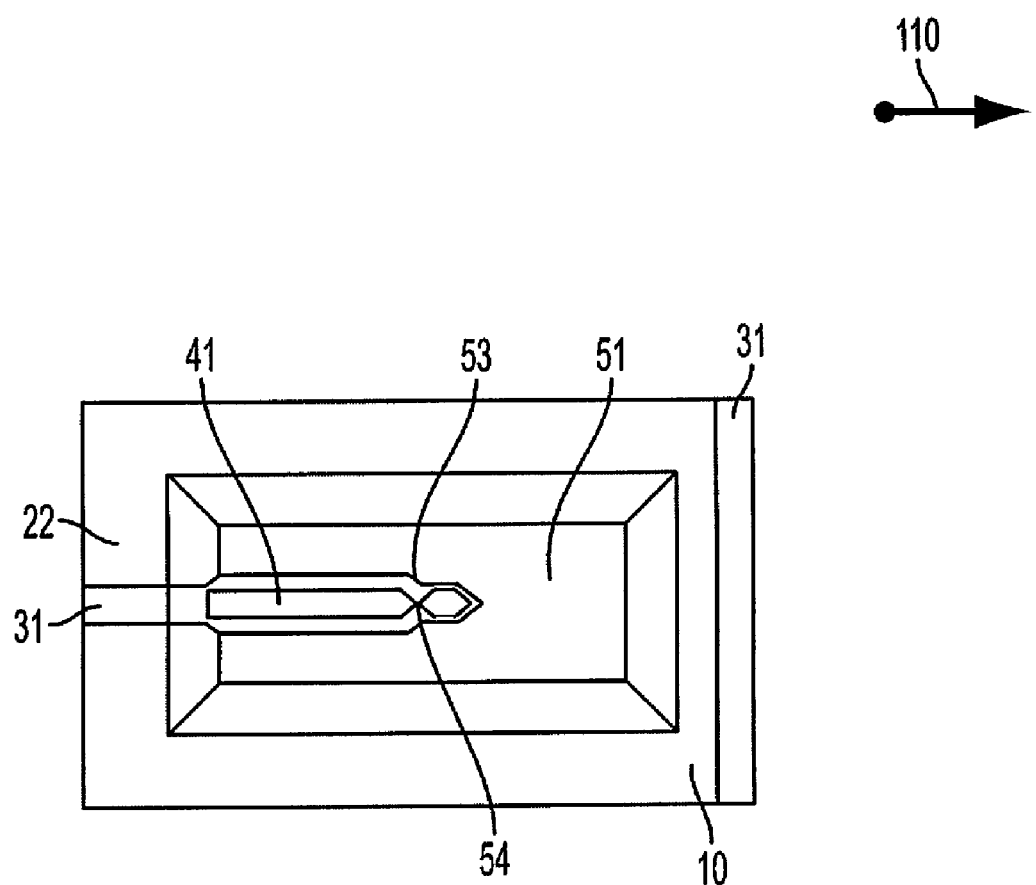
Figure 111:
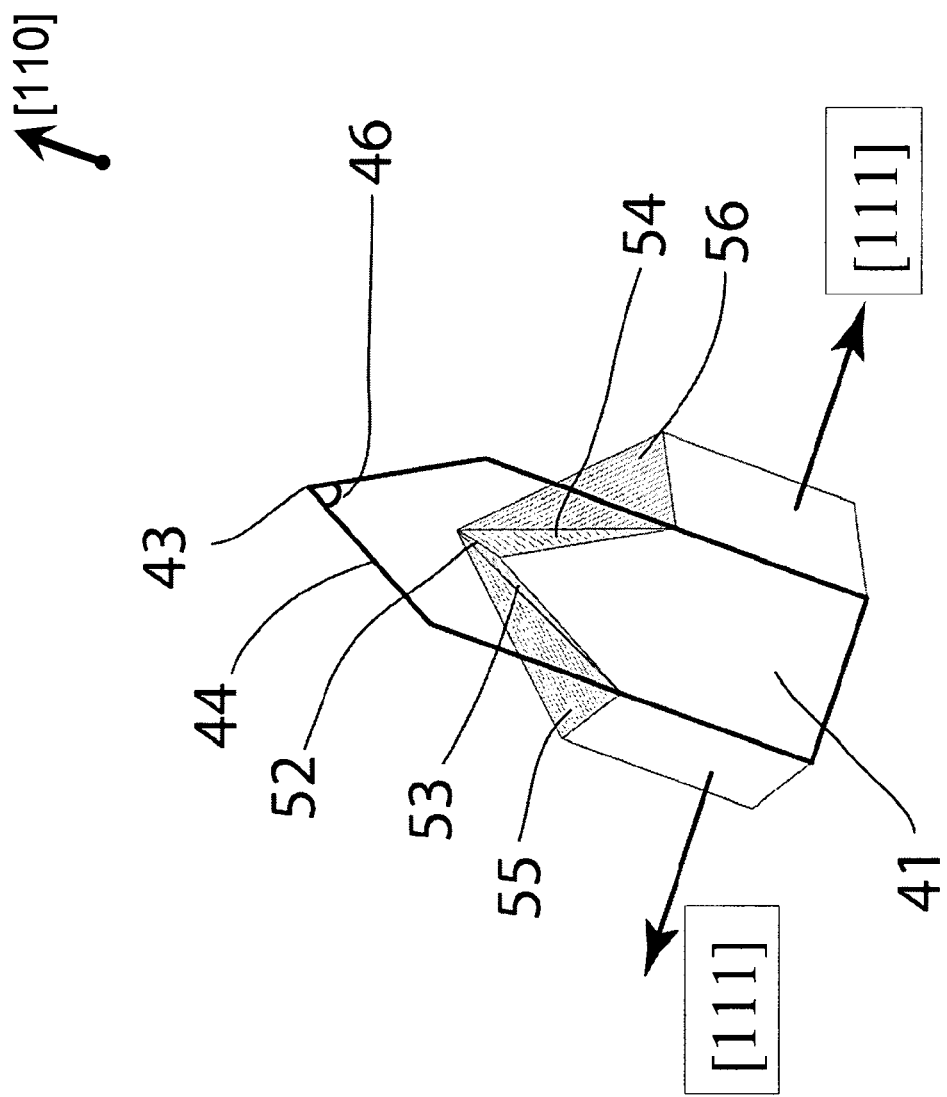
FIG. 111 is an enlarged, bottom-side perspective view of the anisotropic silicon etch with the undercut etch of the silicon nitride cantilever.

FIG. 16 shows a cross-sectional view of the final probe. The silicon handle 22 of the probe, the nitride cantilever 41 and the single crystal silicon tetrahedral three-sided tip 63 are shown.

FIGS. 108A through 111 show cross-sectional, bottom-side plan and enlarged perspective views of another embodiment for producing the high-frequency low-spring constant probes that are the object of the invention. In this embodiment, the processing steps depicted in FIGS. 5A through 11 of the first embodiment, which are in part necessary for formation of the sacrificial oxide extension (45 of FIGS. 9A through 11) are omitted and the processing steps depicted in FIGS. 108A through 111 substituted in their stead. The entire probe fabrication process for this embodiment follows the processing steps of the first embodiment except for the omissions and substitutions just referred to.

Figure 210A:
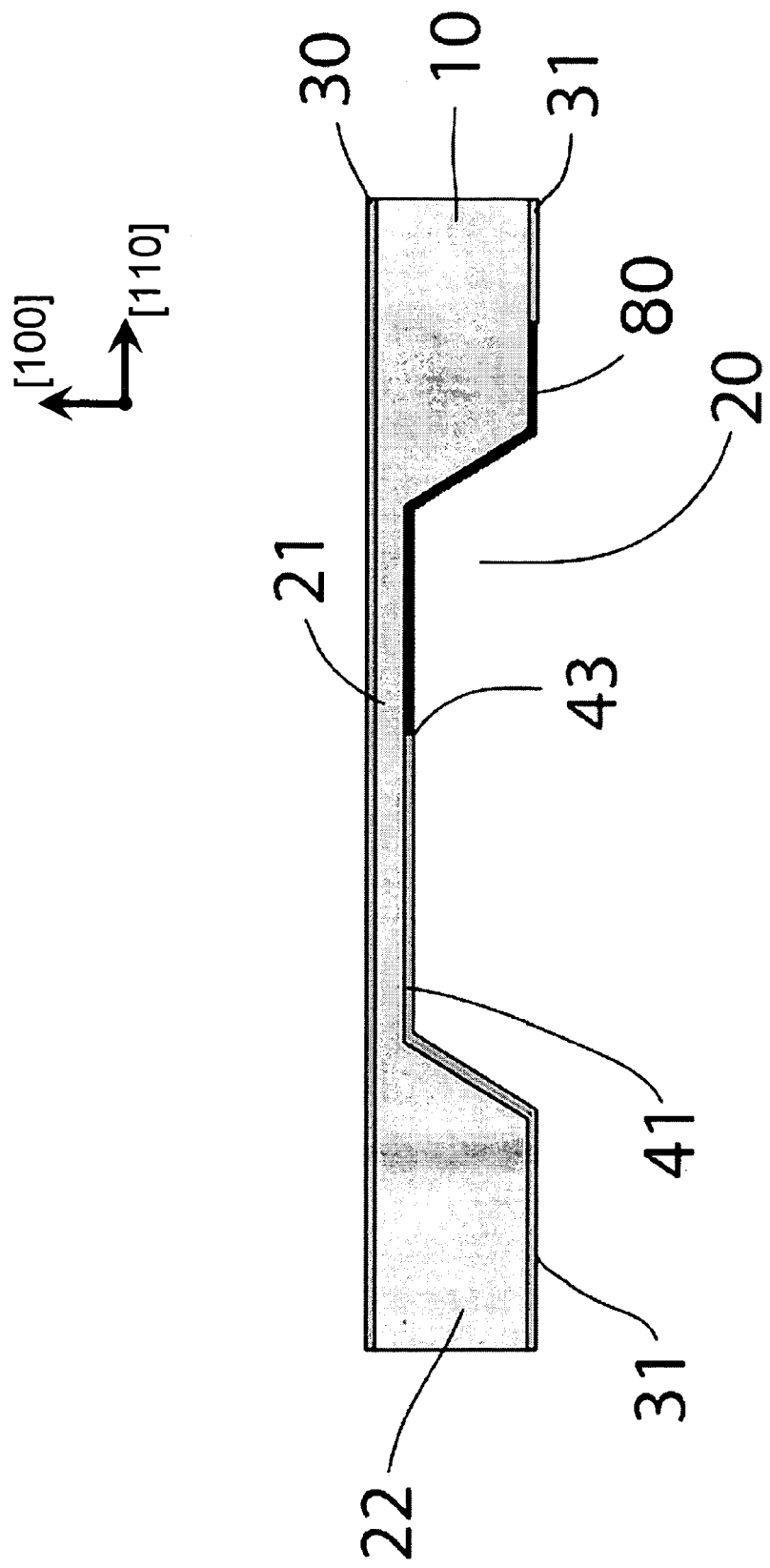
FIGS. 210A and 210B are, respectively, a cross-sectional view and bottom-side plan view of the substrate showing the growth of silicon dioxide on the exposed bottom-side of the silicon substrate surrounding the formed silicon nitride cantilever, which is part of the third embodiment of the present invention.
Figure 210B:
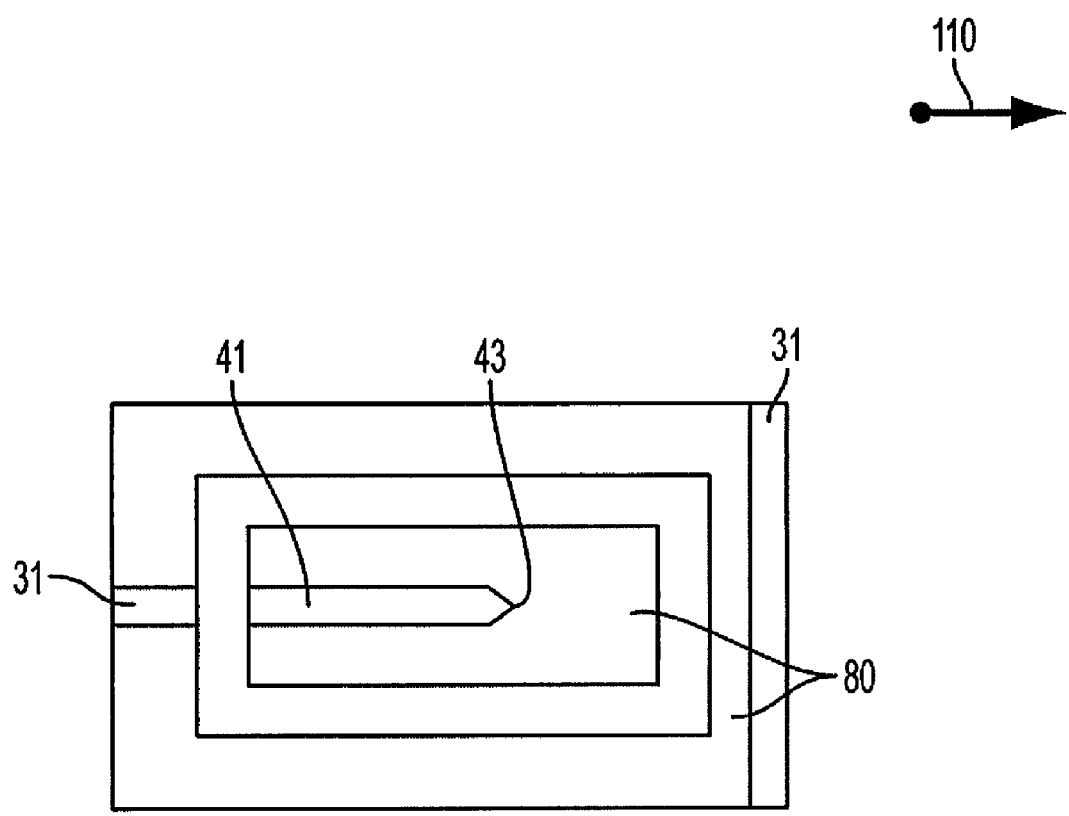
Figure 211:
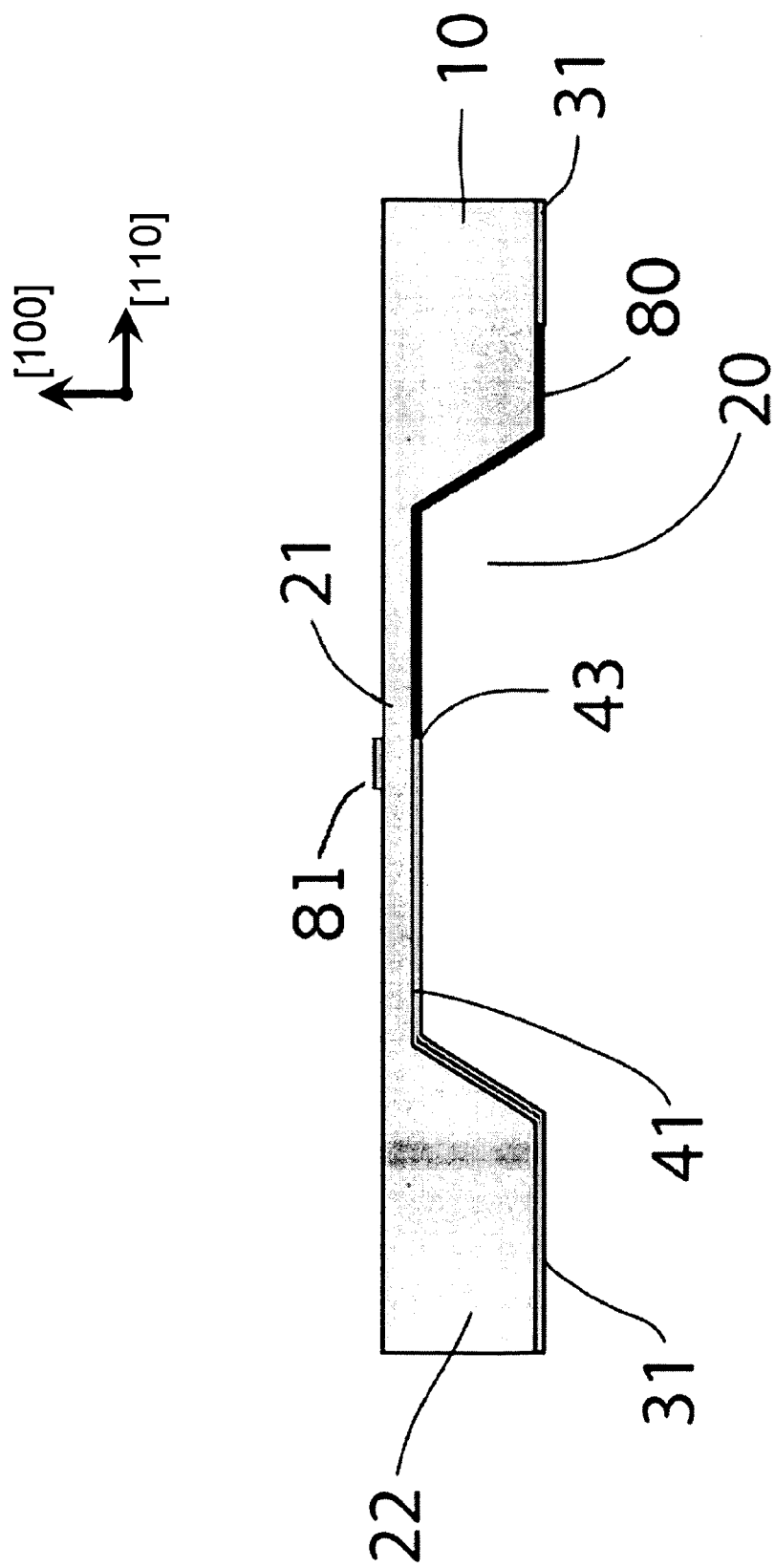
FIG. 211 is a cross-sectional view showing the top-side silicon nitride layer formed into a tip etch mask which is aligned to the end of the silicon nitride cantilever on the bottom-side.
Figure 212A:
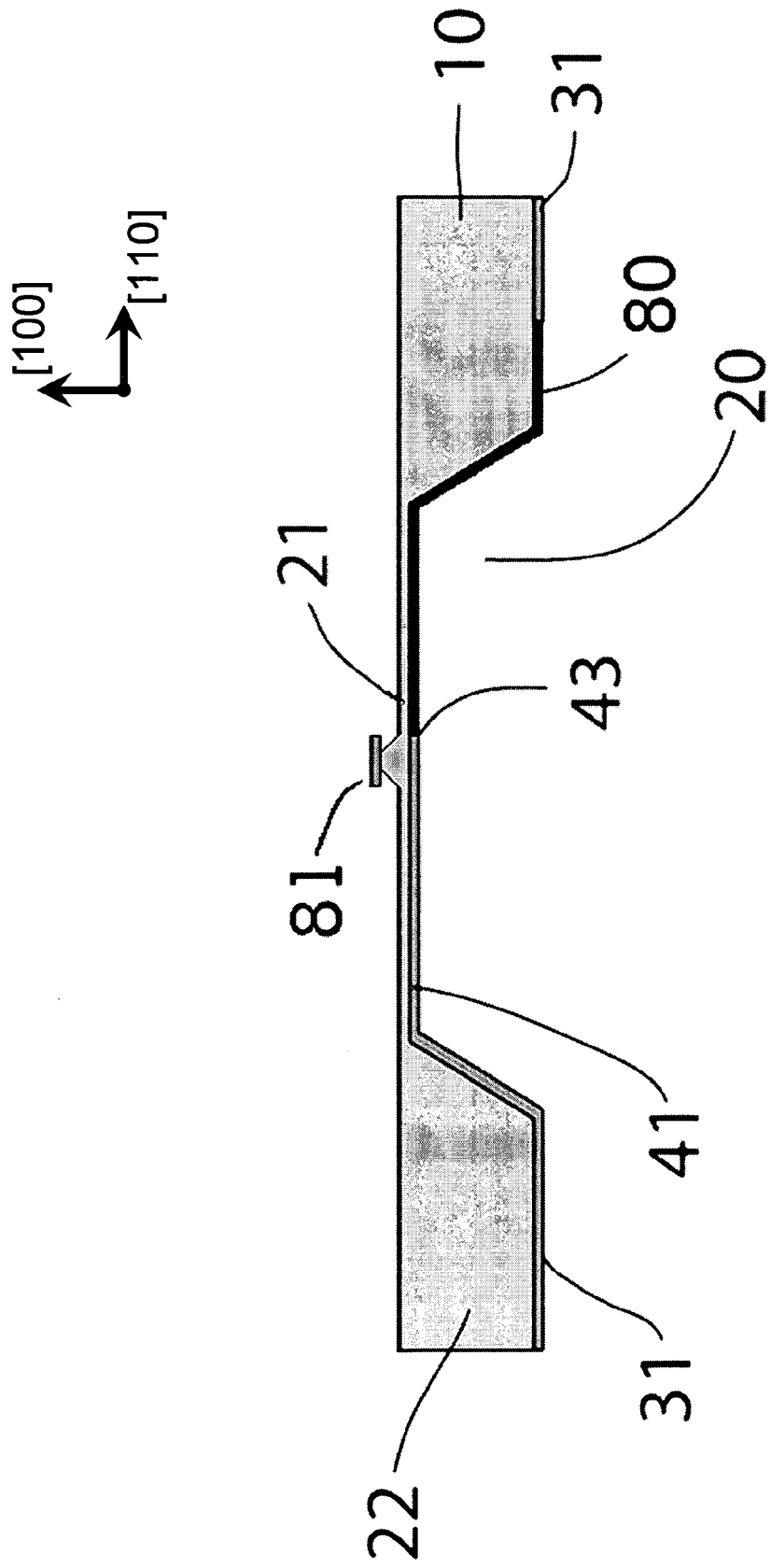
FIGS. 212A and 212B are cross-sectional views showing the forming of a silicon tip by etching the exposed top-side silicon surface and stopping when the silicon membrane is completely removed.
Figure 212B:
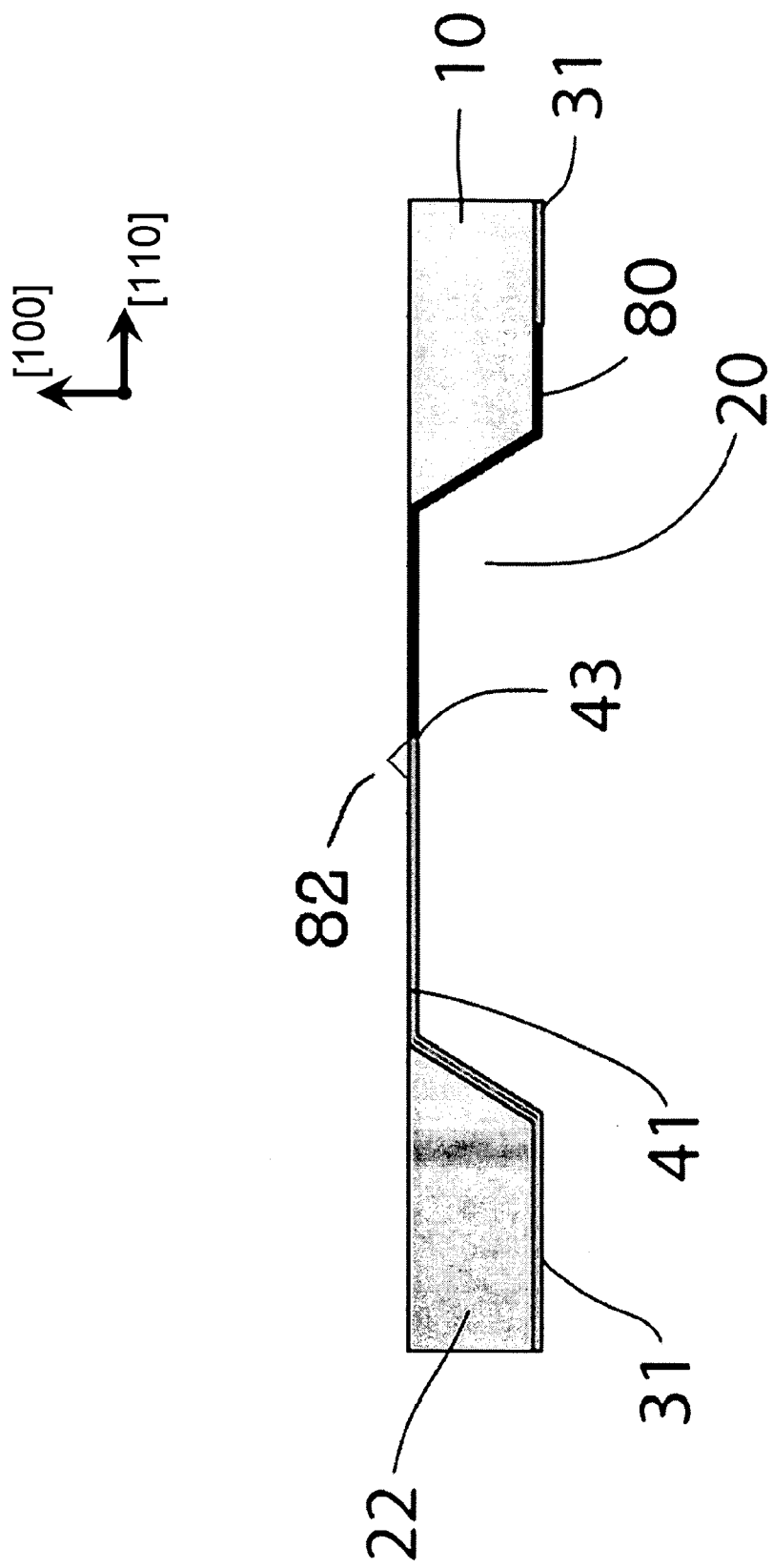
Figure 213:
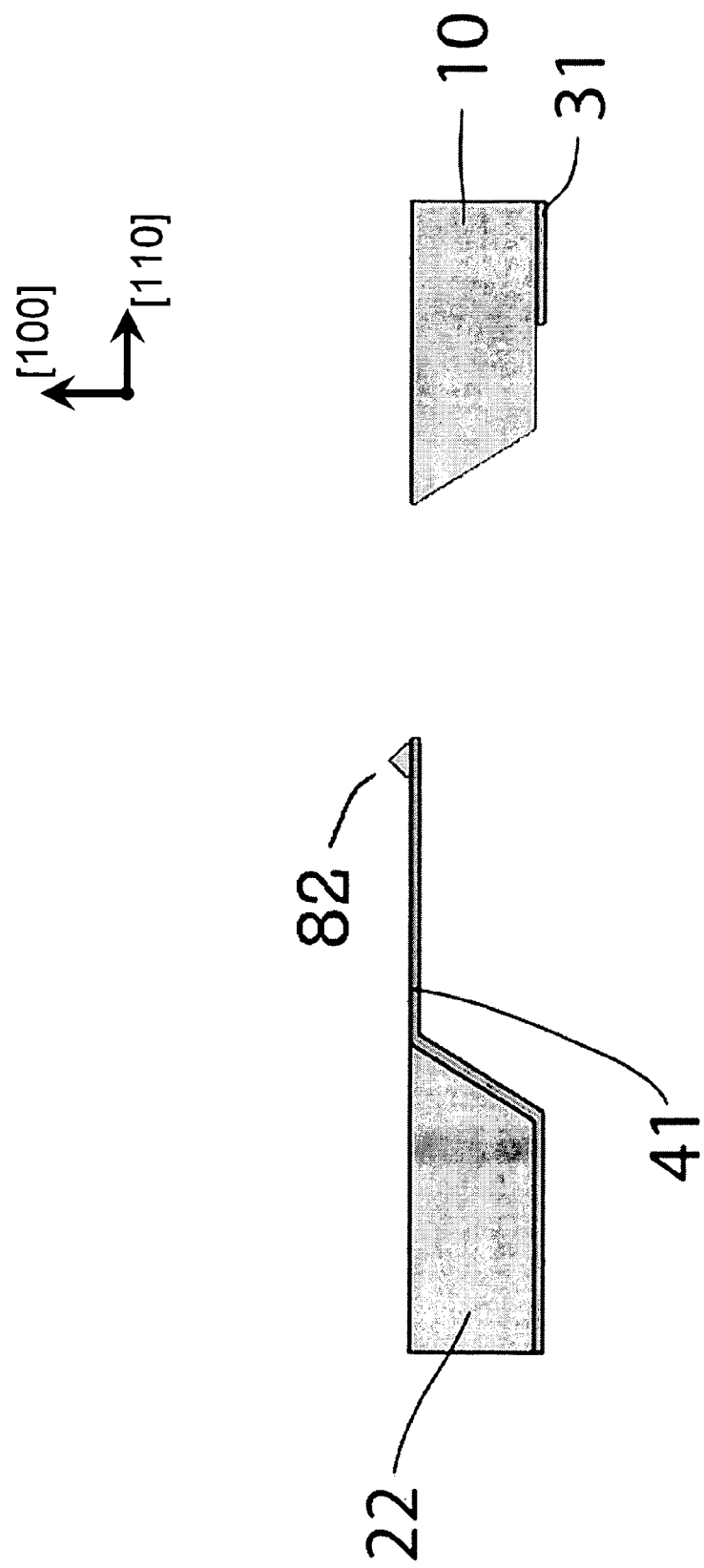
FIG. 213 is a cross-sectional view of the silicon handle, the nitride cantilever, and silicon tip after the removal of the bottom-side oxide.

FIGS. 210A through 213 show cross-sectional and bottom-side plan views of another embodiment for producing the high-frequency low-spring constant probes that are the object of the invention. This embodiment begins with the processing steps depicted in FIGS. 1 through 4 of the first embodiment, followed by the processing steps depicted in FIGS. 108A through 109B of the second embodiment and finished with the processing steps depicted in FIGS. 210A through 213. FIGS. 210A and 210B represent the growth of a silicon dioxide film on the exposed bottom-side silicon resulting from completion of the processing step depicted in FIGS. 109A and 109B. The next step, shown in FIG. 211, is a lithography step on the top-side of the substrate which is aligned with the end of the nitride cantilever 43 on the bottom-side of the substrate. This may be accomplished with a lithography tool known to those skilled in the art. Using the tool and RIE, the nitride layer 30 is formed into a tip mask 81 which is selectively stopped on the silicon membrane 21. The tip mask can be any number of shapes, including circles and polygons with any number of sides. FIGS. 212A and 212B show the etching of the exposed silicon on the top-side of the substrate. The etching can be done with a wet isotropic chemistry, a wet anisotropic chemistry or a plasma RIE. The idea is that any number of different tips shapes which may be useful for different AFM imaging needs can be produced with a tip etch process that is done entirely from the top-side of the silicon substrate. FIG. 213 shows a cross-sectional view of the final probe after any remaining oxide 80 is selectively removed with a wet HF based etchant. The silicon handle 22 of the probe, the nitride cantilever 41 and the single crystal silicon tip 82 are shown.

FIGS. 308A through 311B show cross-sectional, bottom-side plan and enlarged perspective views of another embodiment for producing the high-frequency low-spring constant probes that are the object of the invention. This embodiment is a cantilever optimization technique that may offer benefits for use with AFMs. AFMs often include integrated optical microscopes so that a probe tip can be landed on a specific spot on a sample of interest. This embodiment results in a cantilever with the tip end having a triangular point conforming with the outermost facets of the tip, thereby giving an optimal plan view of the probe which allows an AFM operator to land the tip on a specific spot of the sample.

Figure 308A:
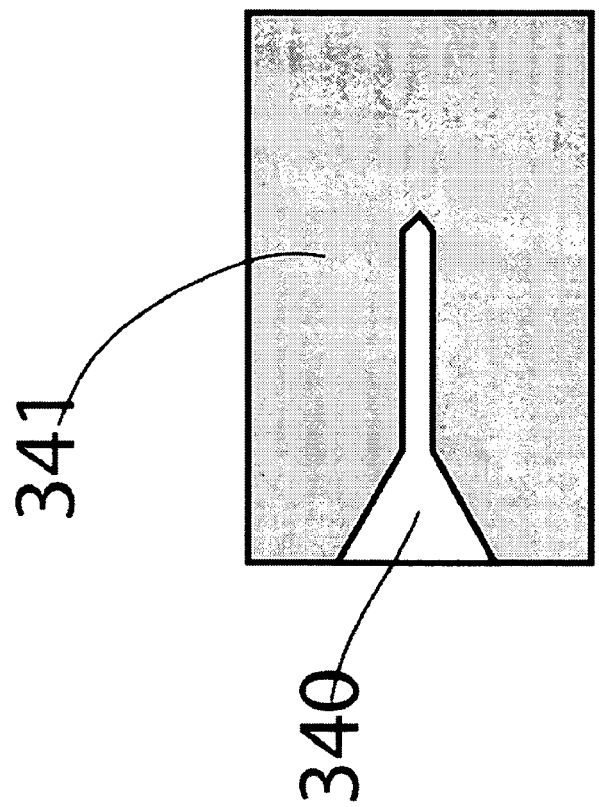
FIG. 308A is a plan view of an optimized cantilever shadow mask with a triangularly shaped handle, which is part of the third embodiment of the present invention.
Figure 308B:
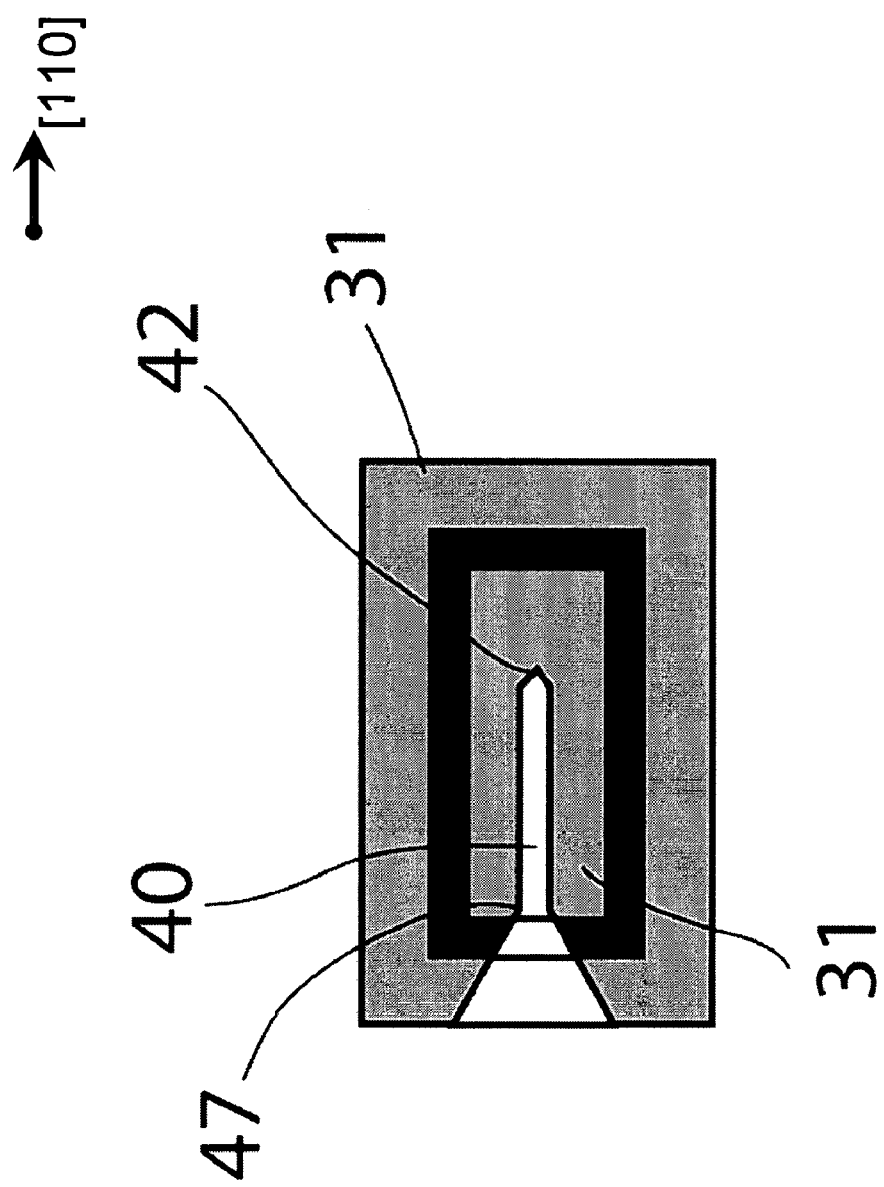
FIG. 308B is a bottom-side plan view of the substrate showing the critical placement of the optimized cantilever etch mask.

FIG. 308A shows a plan view of a shadow mask 341 which will form a cantilever etch mask on the probe substrate. The cantilever shaped aperture 340 in the shadow mask 341 is wide at the base, narrows to a rectangle along its length and terminates in a triangular end. This embodiment begins with the processing steps depicted in FIGS. 1 through 4 of the first embodiment, followed by the processing steps depicted in FIGS. 108A through 110B of the second embodiment, except that here the shadow mask 341 results in the shape 340 depicted in FIG. 308A instead of the shape depicted in FIGS. 108B, 109B and 110B. FIG. 308B shows a bottom-view of the substrate equivalent to that depicted in FIG. 108B which is the result of completing the processing steps referred to in the preceding sentence. FIG. 308B shows a critical alignment 47 with the wide part of the mask landing on the flat underside of the (100) membrane just past the (111) plane of the probe substrate. After completion of the processing step depicted in FIGS. 110A and 110B, this embodiment continues with the processing step shown in FIG. 311 A. In this step, chrome/gold or any other suitable thin film material, is deposited 90 on the bottom-side of the substrate to be used as a shaping etch mask for the cantilever. The substrate can then be exposed to a wet etchant, like hot Phosphoric Acid, or a RIE selective to the cantilever material in order to remove the extraneous overhanging cantilever material. The cantilever material will be removed from any place where there is exposed cantilever film. The chrome/gold layer can then be selectively removed using appropriate chemical etchants.

Figure 311A:
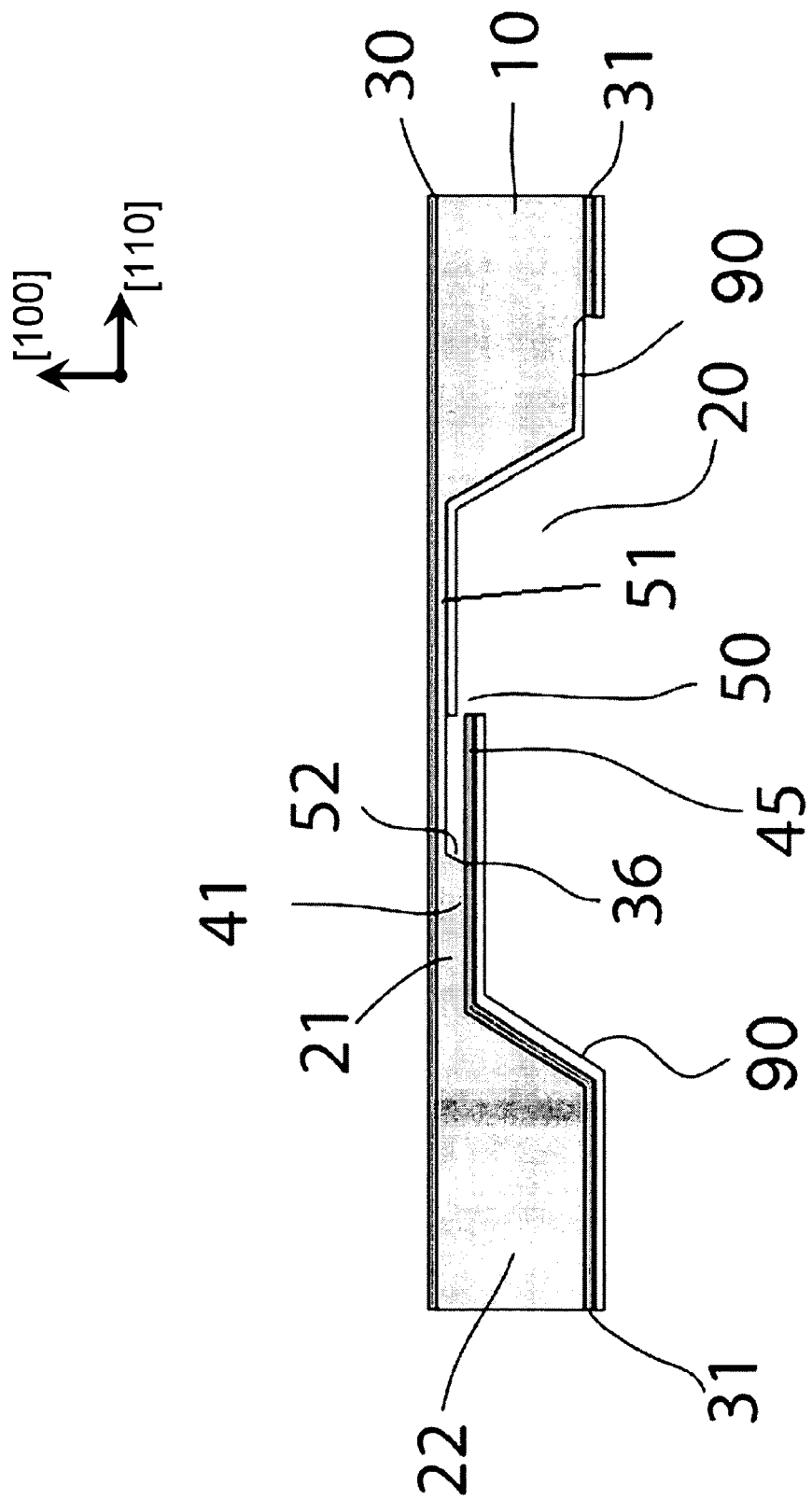
FIG. 311A is a cross sectional view of the substrate showing the deposition of an etch mask layer on the bottom-side for removal of the excessive silicon nitride film.
Figure 311B:
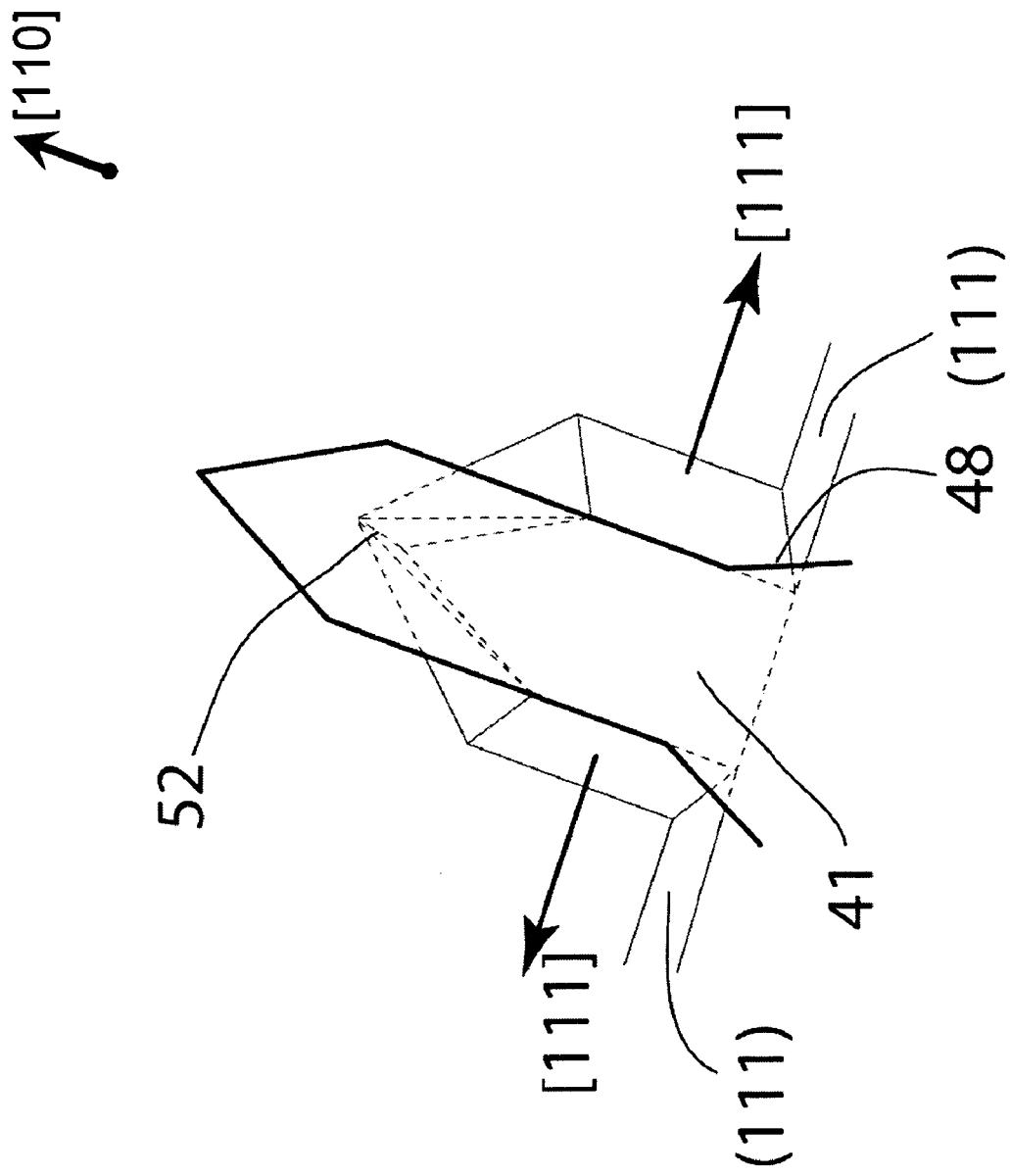
FIGS. 311B and 311C are enlarged, bottom-side perspective views showing the etching of the cantilever to an optimal shape for use with an AFM.
Figure 311C:
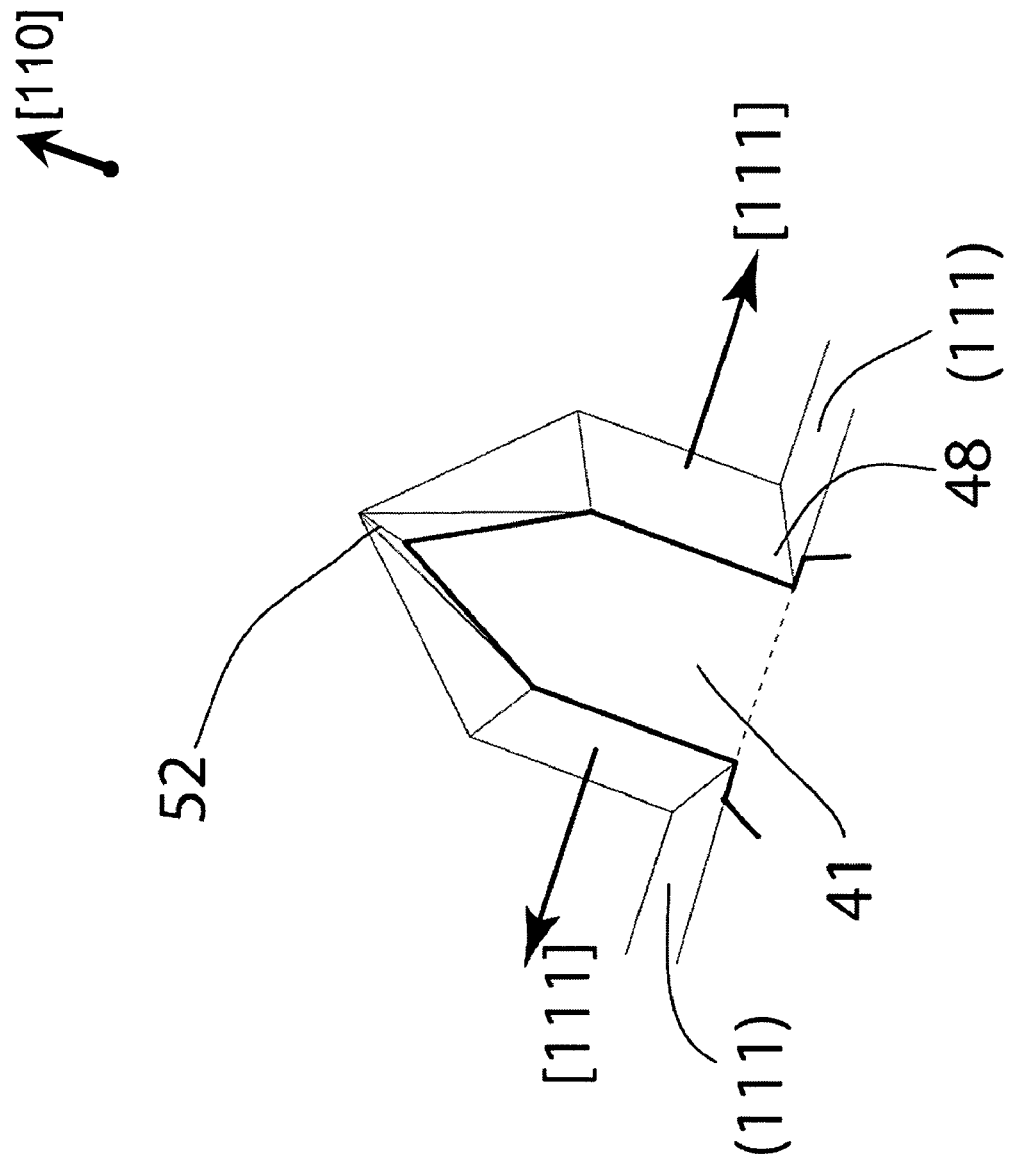
Figure 40I:
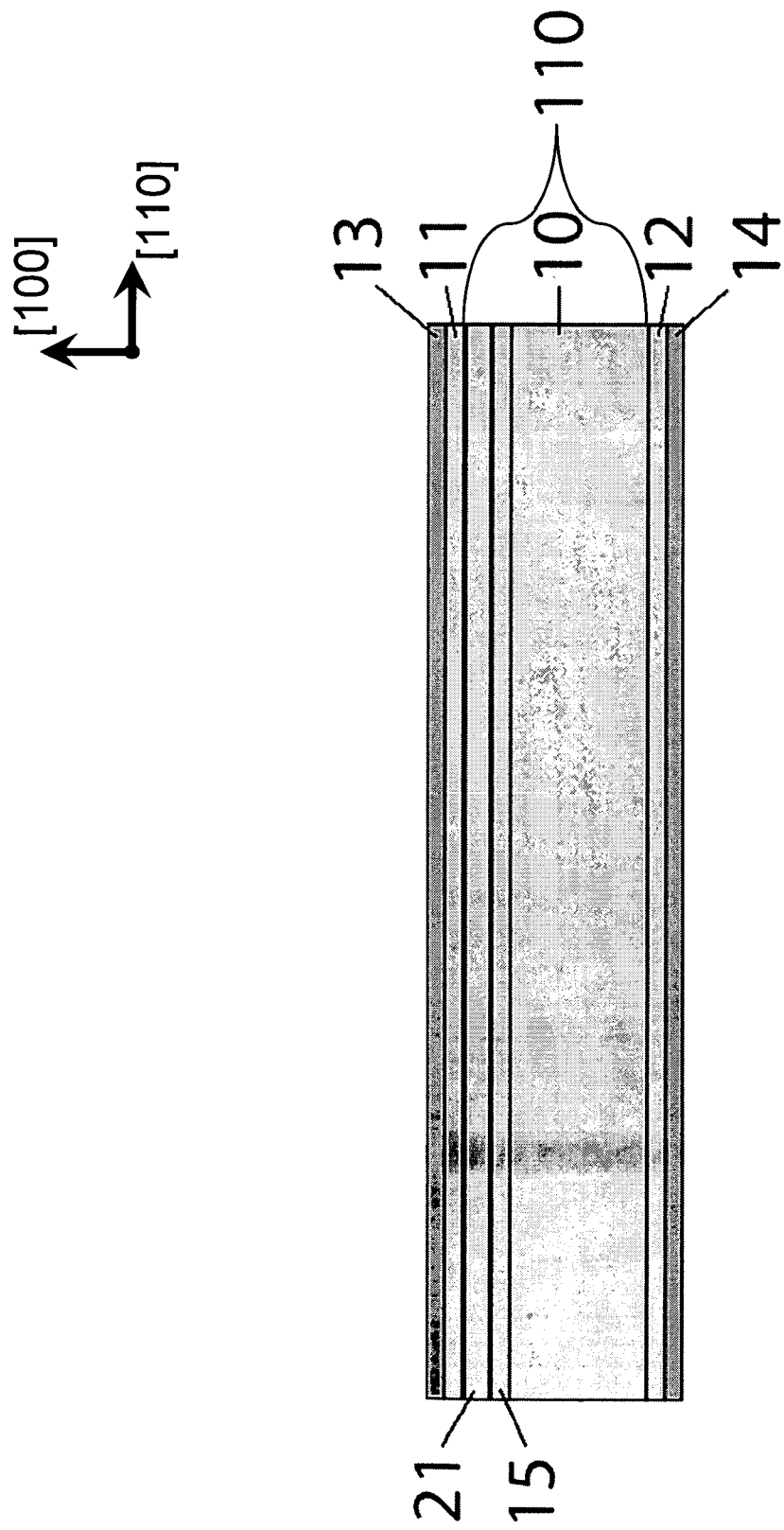

FIGS. 311B and 311C are enlarged bottom-side perspective views of the cantilever material that will be removed during the etch, the former being before the etch and the latter after the etch. The wide portion of the cantilever base 48 that connects to the silicon handle 22 was necessary to prevent the silicon handle from forming erratic undercut etch planes near the cantilever base during the tip etch steps depicted in FIG. 110. If a wide cantilever base was not used, the undercut etch planes would create notches in the cantilever where it extends from the (111) plane of the silicon handle 22, the reason being that arbitrary silicon planes will be exposed when nitride film is removed by RIE during the process step depicted in FIG. 109 due to poor selectivity of nitride to silicon during a RIE.

After completion of the processing steps just outlined, this embodiment is finished with the processing steps depicted in FIGS. 12 through 16.

Figure 402:
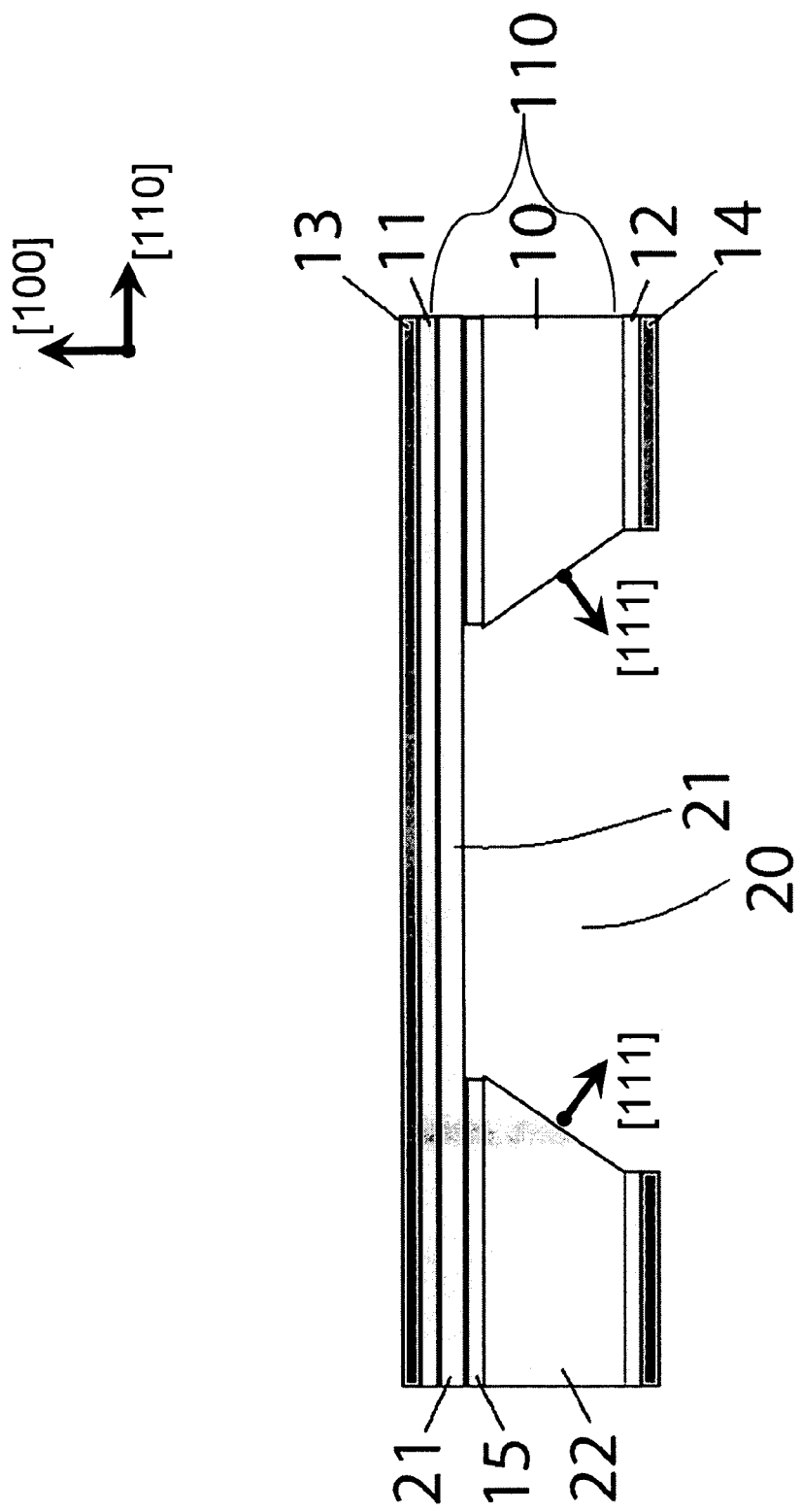
Figure 403:
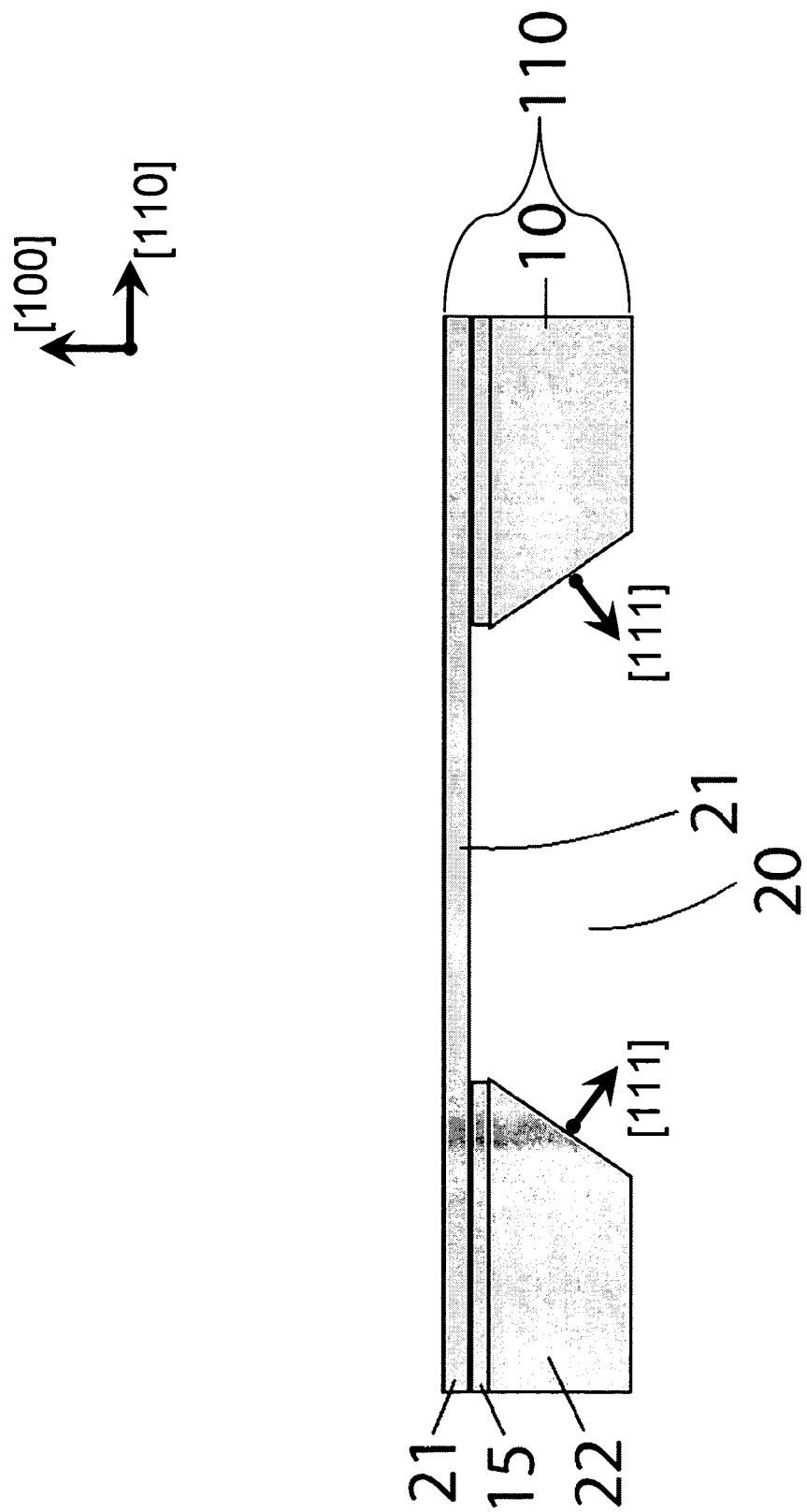

FIGS. 401 through 403 show cross-sectional views of another embodiment for producing the high-frequency low-spring constant probes that are the object of the invention where the starting substrate is a Silicon-on-Insulator (SOI) substrate. This substrate is suitable for all processing steps depicted in any of the previous figures except that a SOI wafer is substituted for the silicon substrate. FIG. 401 shows the starting SOI substrate 110 after oxide films 11 and 12 and nitride films 13 and 14 have been added. Note that the silicon membrane 21 is part of the starting SOI substrate and is separated from the bulk silicon 10 by the oxide insulator 15. FIG. 402 shows the patterning of the bottom-side nitride film 14 and oxide film 12 followed by the wet anisotropic silicon etch. In this case, the wet etch automatically stops when the buried oxide layer 15 is reached. It is the extra oxide layer 15 that is the key advantage to the SOI substrate as it will keep the silicon membrane 21 free of etch defects when compared to the results given by the counterpart processing step depicted in FIG. 2. Etch defects, which are commonplace when wet etching silicon, can propagate thru to the final cantilever surface in standard silicon substrate processing, and adversely affect the probe's performance. FIG. 403 is the SOI counterpart to FIG. 3 where the nitride films 13 and 14 and oxide films 11 and 12 have been removed from the substrate with appropriate acids. Note that the buried oxide insulator layer 15 is not compromised during the oxide etch due to its minimal exposed surface area.

The described embodiments of the present invention are only considered to be preferred and illustrative of the inventive concept. The scope of the invention is not to be restricted to such embodiments. Various and numerous other arrangements may be devised by one skilled in the art without departing from the spirit and scope of the invention.

The invention claimed is:

1. A method of making a probe, comprising:
A) providing a crystalline substrate of a first material having a first side and a second side that is opposite to the first side;
B) forming a first layer over the first side of the substrate, wherein a first side of the first layer is adjacent to the first side of the substrate and a second side of the first layer is opposite to the first side of the first layer;
C) forming a masking layer over a portion of the second side of the first layer; and
D) removing a portion of the substrate from the second side thereof to expose the first layer and to form a tip of the first material connected to the first layer, wherein at least a portion of the first layer forms a cantilever attached to a remaining portion of the substrate.

2. The method of claim 1, wherein the substrate is a silicon substrate and the first material is silicon.

3. The method of claim 1, wherein the first side of the substrate has an uneven surface.

4. The method of claim 1, further comprising patterning the first layer prior to the step of removing.

5. The method of claim 1, wherein the masking layer further covers a portion of a second layer formed on the substrate.

6. The method of claim 5, wherein the first layer and the second layer comprise different materials.

7. The method of claim 6, wherein the substrate comprises silicon, the first layer comprises silicon nitride and the second layer comprises silicon oxide.

* * * * *